(12) United States Patent
Miyake et al.

(10) Patent No.: US 8,309,654 B2
(45) Date of Patent: Nov. 13, 2012

(54) METHOD OF PRODUCING PARTICLE-SHAPE WATER-ABSORBING RESIN MATERIAL

(75) Inventors: Koji Miyake, Okayama (JP); Takahiro Kitano, Himeji (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 395 days.

(21) Appl. No.: 10/933,319

(22) Filed: Sep. 3, 2004

(65) Prior Publication Data

US 2005/0113252 A1 May 26, 2005

(30) Foreign Application Priority Data

Sep. 5, 2003 (JP) ................................ 2003-314625
Sep. 2, 2004 (JP) ................................ 2004-256221

(51) Int. Cl.
*C08F 2/16* (2006.01)
*C08F 20/06* (2006.01)
*C08G 18/62* (2006.01)
*C08G 73/10* (2006.01)
*C08L 67/00* (2006.01)

(52) U.S. Cl. ........ 524/804; 524/832; 524/845; 524/847; 526/317.1

(58) Field of Classification Search .................. 524/804, 524/832, 845, 847; 526/317.1, 930
See application file for complete search history.

(56) References Cited

U.S. PATENT DOCUMENTS

| | | |
|---|---|---|
| 4,093,776 A | 6/1978 | Aoki et al. |
| 4,286,082 A | 8/1981 | Tsubakimoto et al. |
| 4,367,323 A | 1/1983 | Kitamura et al. |
| 4,446,261 A | 5/1984 | Yamasaki et al. |
| 4,625,001 A | 11/1986 | Tsubakimoto et al. |
| 4,683,274 A | 7/1987 | Nakamura et al. |
| 4,734,478 A | 3/1988 | Tsubakimoto et al. |
| RE32,649 E | 4/1988 | Brandt et al. |
| 4,863,989 A | 9/1989 | Obayashi et al. |
| 4,873,299 A | 10/1989 | Nowakowsky et al. |
| 4,972,019 A | 11/1990 | Obayashi et al. |
| 4,973,632 A | 11/1990 | Nagasuna et al. |
| 4,985,518 A | 1/1991 | Alexander et al. |

(Continued)

FOREIGN PATENT DOCUMENTS

EP 0 304 319 A2 2/1989

(Continued)

OTHER PUBLICATIONS

Notice of Opposition dated Apr. 28, 2011 in European Application No. 04021015.5, with English translation.

(Continued)

*Primary Examiner* — William Cheung
(74) *Attorney, Agent, or Firm* — Harness, Dickey & Pierce, P.L.C.

(57) ABSTRACT

A method of producing a particle-shape water-absorbing resin material is realized. With this method, it is possible to prevent deterioration of properties of the particle-shape water-absorbing resin material, and reduces damages onto surfaces thereof. This method is arranged such that (a) water-absorbing resin particles are surface-treated by using a crossing agent so that surfaces of the particles are cross-linked, (b) an additive for giving a function to the particles is added to the particles, (c) and a step of mixing the particles and the additive is carried out in a step of performing particle-size regulating treatment for the particles which includes agglomerated particles.

28 Claims, 3 Drawing Sheets

U.S. PATENT DOCUMENTS

| | | | |
|---|---|---|---|
| 5,002,986 A | 3/1991 | Fujiura et al. | |
| 5,124,416 A | 6/1992 | Haruna et al. | |
| 5,145,906 A | 9/1992 | Chambers et al. | |
| 5,154,713 A | 10/1992 | Lind | |
| 5,229,488 A | 7/1993 | Nagasuna et al. | |
| 5,244,735 A | 9/1993 | Kimura et al. | |
| 5,250,640 A | 10/1993 | Irie et al. | |
| 5,264,495 A | 11/1993 | Irie et al. | |
| 5,275,773 A | 1/1994 | Irie et al. | |
| 5,314,420 A | 5/1994 | Smith et al. | |
| 5,328,935 A | 7/1994 | Van Phan et al. | |
| 5,338,766 A | 8/1994 | Phan et al. | |
| 5,369,148 A | 11/1994 | Takahashi et al. | |
| 5,380,808 A | 1/1995 | Sumiya et al. | |
| 5,409,771 A * | 4/1995 | Dahmen et al. | 428/327 |
| 5,462,972 A | 10/1995 | Smith et al. | |
| 5,610,220 A | 3/1997 | Klimmek et al. | |
| 5,712,316 A | 1/1998 | Dahmen et al. | |
| 5,795,893 A | 8/1998 | Bondinell et al. | |
| 5,981,070 A | 11/1999 | Ishizaki et al. | |
| 5,985,944 A | 11/1999 | Ishizaki et al. | |
| 6,100,305 A | 8/2000 | Miyake et al. | |
| 6,107,358 A | 8/2000 | Harada et al. | |
| 6,124,391 A | 9/2000 | Sun et al. | |
| 6,140,395 A | 10/2000 | Hatsuda et al. | |
| 6,251,950 B1 | 6/2001 | Durden et al. | |
| 6,388,000 B1 | 5/2002 | Irie et al. | |
| 6,444,744 B1 | 9/2002 | Fujimaru et al. | |
| 6,455,600 B1 | 9/2002 | Hahnle et al. | |
| 6,469,080 B2 * | 10/2002 | Miyake et al. | 524/239 |
| 6,559,239 B1 | 5/2003 | Riegel et al. | |
| 6,599,989 B2 | 7/2003 | Wada et al. | |
| 6,667,372 B1 * | 12/2003 | Miyake et al. | 526/61 |
| 6,716,894 B2 | 4/2004 | Kajikawa et al. | |
| 6,720,073 B2 | 4/2004 | Lange et al. | |
| 6,727,345 B2 | 4/2004 | Kajikawa et al. | |
| 2001/0053807 A1 * | 12/2001 | Miyake et al. | 524/239 |
| 2002/0072471 A1 | 6/2002 | Ikeuchi et al. | |
| 2002/0128618 A1 | 9/2002 | Frenz et al. | |
| 2004/0071966 A1 | 4/2004 | Inger et al. | |
| 2004/0180189 A1 | 9/2004 | Funk et al. | |
| 2005/0020780 A1 | 1/2005 | Inger et al. | |
| 2005/0234413 A1 | 10/2005 | Funk et al. | |
| 2007/0149716 A1 | 6/2007 | Funk et al. | |
| 2008/0166410 A1 | 7/2008 | Funk et al. | |

FOREIGN PATENT DOCUMENTS

| | | |
|---|---|---|
| EP | 0 339 461 A1 | 11/1989 |
| EP | 0 493 011 A2 | 7/1992 |
| EP | 0629411 A1 | 12/1994 |
| EP | 1 072 630 A1 | 1/2001 |
| EP | 1 113 037 A2 | 7/2001 |
| JP | 56-133028 | 10/1981 |
| JP | 61-97333 | 5/1986 |
| JP | 7-088171 | 4/1995 |
| WO | WO-00/10619 A1 | 3/2000 |
| WO | WO-01/74913 A1 | 10/2001 |
| WO | WO-03/002623 A1 | 1/2003 |
| WO | WO-2004/018005 A1 | 3/2004 |

OTHER PUBLICATIONS

A1: *Characterization Analysis* of the patent claims of EP 1 512 712 B1, Apr. 27, 2011 (with English translation).

Hammer mill (Technology), http://de.wikipedia.org/wiki/Hammermühle_(Technik), printed Apr. 24, 2011 (with English translation).

Ulshöfer et al., *Mathematical formula collection for secondary school*, Verlag Konrad Wittwer Stuttgart, $3^{rd}$ e.d., p. 4, 1988 (with English translation).

Buchholz et al., *Solution Polymerization*, Modern Superabsorbent Polymer Technology, p. 93, 1997.

*Particle Size Analysis and Characterization of Classification Process: 6. Classification Methods*, Ullmann's Enc. Ind. Chem., $6^{th}$ e.d. (2002) Electronic Release.

* cited by examiner

METHOD OF PRODUCING PARTICLE-SHAPE WATER-ABSORBING RESIN MATERIAL

This Nonprofessional application claims priority under 35 U.S.C. §119(a) on Patent Application No. 2003/314625 filed in Japan on Sep. 5, 2003, and Patent Application No. 2004/256221 filed in Japan on Sep. 2, 2004, the entire contents of each of which are hereby incorporated herein by reference.

FIELD OF THE INVENTION

The present invention relates to a method of producing a water-absorbing resin material (water-absorbing resin composition material) in a particle-shape. More particularly, the present invention relates to a method of producing a water-absorbing resin material in a particle-shape (hereinafter, sometimes material), the method including the step of performing a particle-size regulating treatment of surface-treated particles of water-absorbing resin, and the step of mixing the particles of the water-absorbing resin water-absorbing resin particles with an additive, the step of mixing being carried out in the step of performing the particle-size regulating treatment thereby giving various functions to the water-absorbing resin material in the particle-shape without deterioration of properties thereof.

BACKGROUND OF THE INVENTION

It is well known that aqueous solution polymerization of water-soluble ethylene-based unsaturated monomer gives a polymer in a hydrate gel form (hydrate gel-form polymer), which serves as a water-absorbing polymer. The hydrate gel-form polymer is a gel-form material being semi-solid and highly elastic. In many cases, the hydrate gel-from polymer, which is rarely used without being further processed, is crushed into small pieces (crushing product (fine particles of gel), and then dried and pulverized into particles. The thus dried and pulverized crushing product (particles) of the hydrate gel-form polymer is used as a water-absorbing resin, that is, an absorbent (in other words, gelling agent, solidifying agent) for absorbing an aqueous liquid.

In many cases, the water-absorbing resin is produced in the form of particles (especially as dried particles). In some cases, cross-linking density in a vicinity of surfaces of the water-absorbing resin particles (water-absorbing resin particles) is increased by subjecting the surfaces of the particles to secondary cross-linking treatment with a surface cross-linking agent. This secondary-liking treatment is called as surface cross-linking or surface treatment (for example, see References 1, 3, and 9). The surface treatment further improves water absorbency against pressure, liquid permeability, and water absorbency of the water-absorbing resin particles.

In order to obtain final particles of the water-absorbing resin or a final water-absorbing resin material in a particle-shape, the step of granulating, the step of adding (mixing in) an additive, and/or the like step is performed if necessary (for example, References 1 and 2) after the surface treatment. In some cases, the step of performing a particle-size regulating treatment (that is, pulverizing and/or classifying the particles) is necessary.

In case where the step of performing the surface treatment is performed, water, an aqueous solution, or the like is evaporated off by heating after the surface treatment in which the water, aqueous solution, or the like is used. The evaporation would possibly cause agglomeration of the water-absorbing resin particles. Moreover, the addition of the additive would possibly causes agglomeration of the water-absorbing resin particles with particles of the additive, agglomeration of the particles with each other, or agglomeration of the particles of the additive. Further, granulation is a treatment to intentionally agglomerate (bind the particles) the water-absorbing resin particles by using a binder such as water or the like.

The agglomeration of the water-absorbing resin particles not only deteriorates the particle-shape water-absorbing resin material (particle shape water absorbing resin composition material) in terms of its properties and the like, but also causes the particle-shape water-absorbing resin material to be unacceptable as a final product. Therefore, it is necessary to subject, to the particle-size regulating treatment, the particle-shape water-absorbing resin material that contains agglomerated particles (agglomerations) and/or large-size particles (The agglomerated particles and the large-size particles have a weight-average diameter of 850 μm or larger, for example). Note that the particle-size regulating treatment is a treatment to give the particle-shape water-absorbing resin material a uniform shape and/or a uniform diameter (for example, the particle-shape water-absorbing resin material is given a weight-average diameter of less than 850 μm to pass through a sieve of 850 μm mesh). Generally, the particle-size regulating treatment is carried out by pulverizing and/or classifying the particles or the agglomerations of the particles.

Moreover, there is known arts in which an additive such as an inorganic powder is added to the surface-treated water-absorbing resin particles, for further improving the properties of the water-absorbing resin particles (for example, see References 1, 3 to 8, and 12). It is preferable that the particles of the additive and the water-absorbing resin particles be mixed uniformly in the particle-shape water-absorbing resin material. In order to mix them uniformly, it is suggested adding, for example, silica (particulates of silicone oxide) or the like in the water-absorbing resin particles, so as to facilitate stirring. Many methods and apparatuses for mixing the additive have been suggested, but there has been no method or apparatus that performs the mixing and the particle-size regulating treatment of the particles in combination. According to the method in which the mixing and the particle-size regulating treatment of the particles are performed in combination, silica or the like is added into the water-absorbing resin particles after the particle-size regulating treatment. Therefore, it is expected that it is possible to uniformly mix the water-absorbing resin particles whose particle size has been regulated by the particle-size regulating treatment.

Moreover, generally, the water-absorbing resin particles are produced by continuous process in which a number of steps are continuously performed (for example, see References 10 to 11).

Reference 1: Japanese Publication of Patent Application, Tokukaisho, publication No. 61-97333 (published on May 15, 1986) which corresponds to the specification of the U.S. Pat. No. 4,734,478;

Reference 2: the Specification of U.S. Pat. No. 5,369,148;
Reference 3: the Specification of U.S. Pat. No. 5,981,070;
Reference 4: the Specification of U.S. Pat. No. 5,797,893;
Reference 5: the Specification of U.S. Pat. No. 5,985,944;
Reference 6: the Specification of U.S. Pat. No. 5,229,488;
Reference 7: the Specification of U.S. Pat. No. 6,124,391;
Reference 8: the Specification of published U.S. Patent application No. 2002/0128618 A1;
Reference 9: the Specification of U.S. Pat. No. 5,610,220;
Reference 10: the Specification of U.S. Pat. No. 6,727,345;
Reference 11: the Specification of U.S. Pat. No. 6,716,894; and Reference 12: the Specification of U.S. Pat. No. 6,720,073.

However, it has found out that, even if the properties of the water-absorbing resin particles are improved by the surface treatment, the addition of the additive results in deterioration of the properties of the particle-shape water-absorbing resin material or failure in sufficiently improving the properties. As a result of intensive studies to find out the reason for the deterioration of the properties of the resultant particle-shape water-absorbing resin material in the method in which the additive is added to the surface-treated water-absorbing resin particles, attention is focused on the particle-size regulating treatment, which has been carried out conventionally by necessity.

The step of performing the particle-size regulating treatment for the particles, which include the agglomerated particles (agglomeration), of water-absorbing resin is a step for converting the agglomerated water-absorbing resin particles into primary particles thereof substantially or mostly. Meanwhile, the step of mixing is a step for mechanically stirring the particles of the water-absorbing resin. (Note that the agglomerations are agglomerated primary particles and have interfaces between the particles, and the primary particles are non-granulated or non-agglomerated single particles, which are obtained by drying a polymer and then, if necessary pulverizing and or classifying the thus dried polymer.) The studies demonstrate that both the step of performing the particle-size regulating treatment and the step of mixing give damages on the surfaces of the water-absorbing resin particles and/or the additive. Even if the water-absorbing resin particles have been subjected to the surface treatment, the damages on the surfaces would possibly reduce effects of the surface treatment in the arrangement in which the mixing is followed by the particle-size regulating treatment.

In other words, it was found that, if the step of mixing the additive such as silica or the like is carried out after the step of performing the particle-size regulating treatment of the water-absorbing resin particles, the surfaces of the water-absorbing resin particles are damaged not only by the particle-size regulating treatment but also the mechanical energy applied thereon in mixing. Whereby, the water-absorbing resin particles as a final product has poor properties undesirably.

On the other hand, it is an option to add silica to the water-absorbing resin particles before subjecting the water-absorbing resin particles to the particle-size regulating treatment. The addition of silica makes the stirring more effective. In this arrangement, however, the uniform mixing cannot be attained. Specifically speaking, because silica is added to the water-absorbing resin particles before the particle-size regulating treatment, silica is not uniformly mixed with the water-absorbing resin particles whose particle size has been regulated by the particle-size regulating treatment, even if it is uniformly mixed with the water-absorbing resin particles before the particle-size regulating treatment. Thus, the sufficient effect of the stirring cannot be attained. Therefore, in general, it is not practical to perform the particle-size regulating treatment of the water-absorbing resin particles after adding the silica therein.

Further, an art has been suggested in which silica is added to the water-absorbing resin particles that have not been subjected to the surface treatment, and then the particles with silica are subjected to crushing (for example, see References 1 and 2). In this art, silica is added to the water-absorbing resin particles in the granulation, for the purpose of giving the water-absorbing resin particles a larger weight-average diameter. That is, this art has no technical idea to uniformly mix silica and the water-absorbing resin particles, or to give various functions to the water-absorbing resin particles. Therefore, it is impossible to apply this art to the surface-treated water-absorbing resin particles.

SUMMARY OF THE INVENTION

In order to solve the aforementioned problems, an object of the present invention is to realized a method of capable of producing a particle-shape water-absorbing resin material without significantly damaging surfaces of particles of the particle-shape water-absorbing resin material, thereby avoiding deterioration of property thereof. The method according to the present invention attains the object by performing the step of mixing an additive, and surface-cross-linked water-absorbing resin particles, especially surface-cross-linked particles, which include agglomerations (agglomerated particles), in the step of performing a particle-size regulating treatment for the particles.

The inventors of the present inventions, as a result of intensive studies to solve the aforementioned problems, found out that a way of mixing and a mixing time are important factors in a method of adding and mixing the additive to the surface-cross-linked particles. The present invention is accomplished based on this finding.

Moreover, the inventors found that the way and time of mixing the additive and the particles have large influences on absorbing property of the particle-shape water-absorbing resin material produced from the particles. The inventors found out that it is preferable to perform the mixing the particles and the additive and the particle-size regulating treatment together (concurrently) (that is, the mixing is performed in (during) the particle-size regulating treatment). Moreover, it was found out by the inventors that the aforementioned problem can be solved by setting the mixing time to an unexpectedly short period, namely, 10 minutes or shorter, in consideration of the conventional arts (especially, from an actual factory-scale production, for example, production per production line (apparatus) of 50 kg/hr or more, 100 kg/hr or more, 500 kg/hr or more, or especially 1 ton/hr or more), on the contrary to such conventional common sense that longer mixing is able to mix the particles and the additive more uniformly to attain high property.

In general, in a manufacturing plant for the water-absorbing resin particles, various reaction apparatuses and processing apparatuses are connected via intermediate process devices for performing transportation and/or storage of the particles. Therefore, As the plant scale is larger, the longer mixing and particle-size regulating treatment are needed. Conventional manufacturing plants of a general production scale (of Metric tons to several ten metric tones per year) are generally designed such that each step has a retention time in a range of from several ten minutes to 1 hour (or to several hours in some cases). The present invention is based on the idea that it is important to design that the time spent in some particular steps among the large number of steps is short, in order to attain water-absorbing resin particles having excellent properties.

Specifically, a first producing method according to the present invention is so arranged that the step of mixing the particles and the additives, and the step of performing the particle-size regulating treatment (pulverizing and/or classification) are carried out together (concurrently). A second producing method according to the present invention is so arranged that the particle-size regulating treatment are performed within 10 minutes or shorter in total.

Specifically, in order to solve the problems, the first method, of the present invention, of producing a particle-shape water-absorbing resin material, includes the steps of: (A) performing surface treatment in which surfaces of water-absorbing resin particles are cross-linked by using a cross-linking agent; (B) performing a particle-size regulating treatment for the surface-treated particles; (C) adding an additive to the surface-treated water-absorbing resin particles; and (D) mixing the additive and the particle, the step (D) being performed in the step (B).

With this arrangement of the first method, in which the step (D) is performed in the step (B) (that is, steps (B) and (D) are performed together (concurrently), it is possible to perform the steps (B) and (D) in one operation. That is, it is possible to perform the particle-size regulating treatment for the surface-treated water-absorbing resin particles, and the mixing of the particle and the additive, together (concurrently).

Moreover, by adding the additive to the particles, it is possible to give the particles a function of various kinds, for example. Further the mixing causes the particles and the additive to be mixed more uniformly. Because of the mixing, the additive can give the particles the function more efficiently.

Further, because the steps (B) and (D) are performed together, it is possible to reduce damage on the surfaces of the particles due to mechanical energy applied thereon from the apparatus for performing the mixing and the particle-size regulating treatment. This makes it possible to attain a particle-shape water-absorbing resin material having the function of various kinds without deteriorating its property.

Furthermore, in order to solve the problems, the second method, of the present invention, of producing a particle-shape water-absorbing resin material, includes the steps of: (A) performing surface treatment in which surfaces of water-absorbing resin particles are cross-linked by using a cross-linking agent; (B) performing a particle-size regulating treatment for the surface-treated particles; (C) adding an additive to the surface-treated water-absorbing resin particles; and (D) mixing the additive and the particle, the step (B) and the step (D) being performed within 10 minutes in total (the step (B) and the step (D) being carried out together or separately (preferably together).

With this arrangement of the second method in which the step (B) and the step (D) are performed within 10 minutes in total, it is possible to shorten the time spent for the particle-size regulating treatment and the mixing. Moreover, by adding the additive to the particles, it is possible to give the particles a function of various kinds, for example. Further the short-time mixing causes the particles and the additive to be mixed so as to have a unexpectedly higher property (e.g. higher liquid permeability, higher blocking property and the like) than the conventional long-time mixing (that is for attaining uniform mixing). Because of the mixing, the additive can give the particles the function more efficiently. Further, because the particle-size regulating treatment and the mixing are performed in a short time, it is possible to reduce damage on the surfaces of the particles, and the additive due to mechanical energy applied thereon from the apparatus for performing the mixing and the particle-size regulating treatment. This makes it possible to attain a particle-shape water-absorbing resin material having the function of various kinds without deteriorating its property.

For a fuller understanding of the nature and advantages of the invention, reference should be made to the ensuing detailed description taken in conjunction with the accompanying drawings.

DESCRIPTION OF THE EMBODIMENTS

Figure 1:
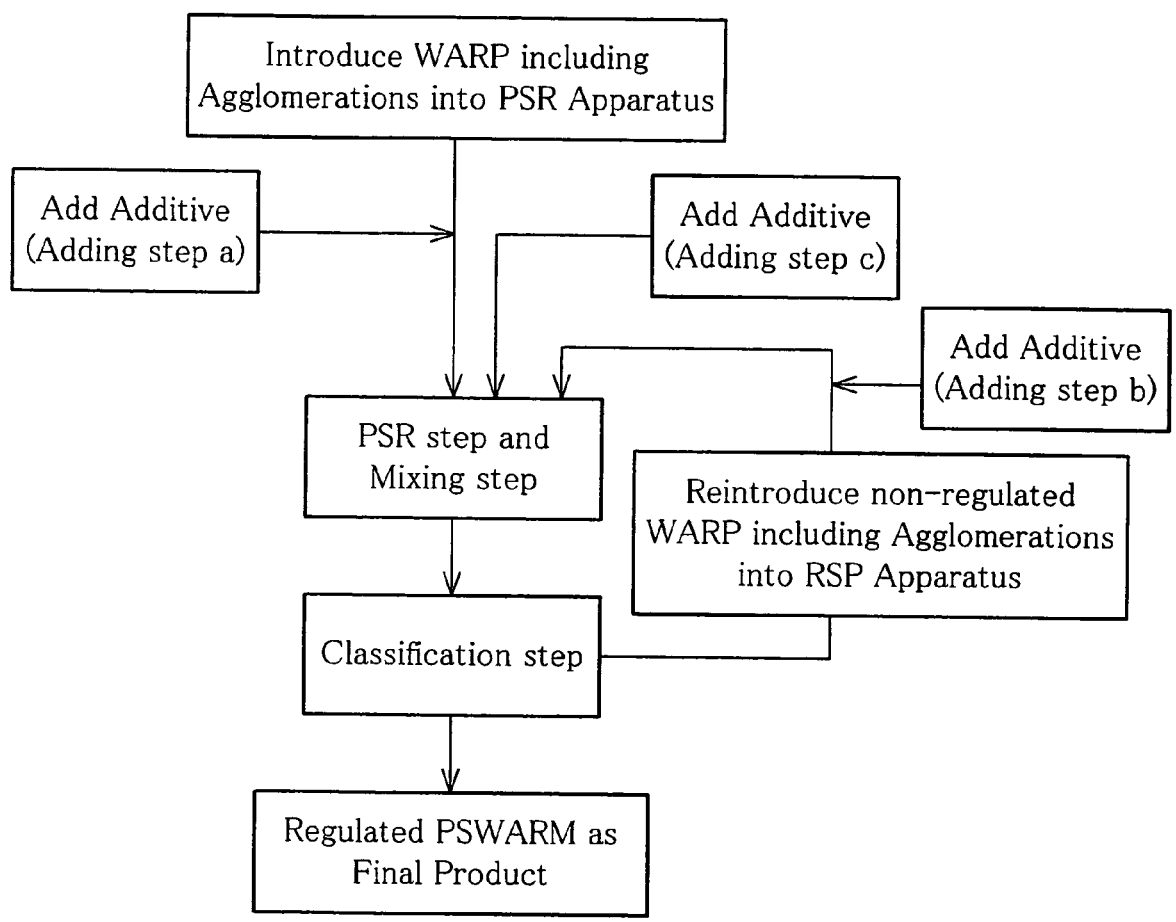
FIG. 1 is a flow chart schematically illustrating a method of producing a particle-shape water-absorbing resin material according to an embodiment of the present invention.

Described below is one embodiment according to the present invention. It should be noted that the present invention is not limited to this. A method, of the present invention, of producing a particle-shape water-absorbing resin material is a method for obtaining, by performing addition of an additive such as an inorganic powder, organic powder, or the like, to surface-treated particles of water-absorbing resin, in particle-size regulating treatment for eliminating agglomerations among the surface-treated particles of the water-absorbing resin, a particle-shape water-absorbing resin material that has various functions without deteriorating its properties.

(I) Water-Absorbing Resin Particles, and Polymerization and Drying

Particles of the water-absorbing resin according to the present invention is a cross-linked polymer having water-swelling property and water-insolubility. For example, the particles are produced by crushing a hydrate gel cross-linked polymer, which is a precursor thereof. The hydrate gel cross-linked polymer can be obtained through aqueous solution polymerization or reverse-phase suspension polymerization, preferably through the aqueous solution polymerization. The water-swelling property is a property to have a water absorbency (CRC; specified in Example) of 5 g/g or more. The water-insolubility is a property to have a water-soluble polymer content (specified in U.S. reissue Pat. RE No. 32,649) of 0% to 40% by weight, preferably of 25% by weight or less, more preferably of 15% by weight or less.

An ethylene-based unsaturated monomer, which is used as a raw material of the hydrate gel cross-linked polymer, is a monomer having a water soluble property (1 g or more, preferably, 10 g or more of the monomer can be solved in 100 g of water at room temperatures and under atmospheric pressure). Specific examples includes: acid radical-containing monomers and their alkali metal salts, alkali earth metal salts, ammonium salts, and alkylamine salts, such as (meth)acrylate, β-acryloyloxypropyonic acid, maleic acid, maleic anhydrate, fumaric acid, chrotonic acid, itaconic acid, cinnamic acid, 2-(meth)acryloylethanesuflonic acid, 2-(meth)acrylolypropanesulfonic acid, 2-(meth)acrylamide-2-methylpropanesulfonic acid, vinylsulfonic acid, stylenesulfonic acid, acrylsulfonic acid, vinylphosphonic acid, 2-(meth)acryloyloxyethylenphosphoric acid, (meth)acryloxy alkanesulfonic acids, and the like; dialkylaminoalkyl(meth)acrylates and their quaternary compound (for example, products from reaction thereof with alylhydlide, products from reaction thereof with dialkyl sulfuric acid, and the like reactants) such as N,N-dimethylaminoethyl(meth)acrylate, N,N-dimethylaminopropyl(meth)acrylate), N,N-dimethylaminopropyl(meth)acrylamide, and the like; dialkylaminohydroxyalkyl(meth)acrylates and their quaternary compounds N-alkylvinylpyridiniumhalides; hydroxyalkyl(meth)acrylates such as hydroxymethyl(meth)acrylate, 2-hydroxydethylmethacrylate, 2-hydroxypropyl(meth)acrylate and the like; acrylamide, methacrylamide, N-ethyl(meth)acrylamide, N-n-propyl(meth)acrylamide, N-isopropyl(meth)acrylamide, N,N-dimethyl(meth)acrylamide; alkoxypolyethyleneglycol(meth)acrylates and polyethyleneglycolmono(meth)acrylates such as 2-hydroxyethyl(meth)acrylate, 2-hydroxypropyl(meth)acrylate, methoxypolyethyleneglycol(meth)acrylate, and the like; vinylpyridine, N-vinylpyridiene, N-vinylpyrrolidone, N-acryloylpiperidine; N-viniyacetoamides; and the like, Those ethylene-based unsaturated monomers may be used solely or two or more of them may be used in appropriate combination.

Among the ethylene-based unsaturated monomers listed above, the monomers containing, as their main component, an acrylate-based monomer (preferably by 50 mol % to 100 mol %, more preferably by 80 mol % to 100 mol %), are preferable, because the use of them gives a hydrate gel-form a higher water absorbing property and a better safety. Here, acrylate-based monomers means bases of acrylic acid and/or aqueous salts of acrylic acid.

Moreover, the aqueous salts of acrylic acid means alkali metal salts, alkali earth metal salts, ammonium salts, hydroxyammonium salts, amine salts, and alkylamine salts, of acrylic acid, the salts having a neutralization ratio (an amount of neutralized acid radical-containing monomer over the total amount of acid radical-containing monomer) in a range of from 30 mol % to 100 mol %, preferably in a range of from 50 mol % to 99 mol %. The preferable acrylic acid and its salt are also exemplified in U.S. Pat. Nos. 6,388,000 and 6,444,744, for example.

These acrylate-based monomers may be used solely or two or more of them may be used in combination. Note that there is no particular limit in terms of an average molecular weight (degree of polymerization) of the water-absorbing resin particles. However, in general, Mw (weight-average molecular weight) is 100,000 or more, preferably 100,000,000 or more, to a measurable limit (unmeasurable level).

The hydrate gel-form cross-linked polymer may be obtained by polymerizing, in the presence of a cross-linking agent, a monomer composite containing, as its main component, an ethylene-based unsaturated monomer listed above. The monomer composite, however, may contain another monomer (copolymerizable monomer) in such an amount that the amount of the copolymerizable monomer does not adversely affect hydrophilic property of the resultant hydrate gel-form cross-linked monomer. The copolymerizable monomer is a monomer which can be copolymerized with the ethylene-based unsaturated monomer.

Specifically, the copolymerizable monomer may be, for example, acrylic esters such as methyl(meth)acrylate, ethyl (meth)acrylate, butyl(meth)acrylate, and the like; hydrophobic monomers (having such a solubility that 0 to 1 g thereof can be dissolved in 100 g of water at room temperature and under atmospheric pressure) such as vinyl acetate, vinyl propyonic acid, and the like; and the like. These copolymerizable monomers may be used solely, or two or more of them may be used in appropriate combination.

Moreover, the cross-linking agent (also called as internal cross-linking agent) for use in polymerization of the monomer component (monomer composite) may be a compound having a plurality of vinyl groups in its molecule; a compound having in its molecule a plurality of functional groups that is reactive with a carboxyl group or a sulfonic acid group; and the like. These cross-linking agents may be used solely, or two or more of them may be used in combination. Note that the cross-linking agent may be added wholly or step by step.

Specific examples of the compound having a plurality of vinyl group in its molecule are: N,N'-methylenebis(meth) acrylamide poly)ethyleneglycoldi(meth)acrylate (poly)propyleneglycoldi(meth)acrylate trimethylolpropanetri(meth) acrylate, trimethylolpropanedi(meth)acrylate, glycerictri (meth)acrylate, glycericacrylatemethacrylate, ethyleneoxide denatured trimethylopropanetri(meth)acrylate, pentaerythritoltetra(meth)acrylate, dipentaerythritolhexa(meth)acrylate, N,N-diallylacrylamide, triallylcyanurate, triallylisocyanurate, triallylphosphate, triallylamine, diallyloxylacetic acid, bis(N-vinylcarboxylic amide), tetraallyloxyethan, and the like.

Examples of the compound having in its molecule, a plurality of functional groups that are reactive with a carboxylic group or a sulfonic group are: multivalent alcohol compounds such as (poly)ethyleneglycol, diethyleneglycol, propyleneglycol, triethyleneglycol, tetraethyleneglycol, 1,3-propanediol, dipropyleneglycol, 2,2,4-trimethyl-1,3-pentanediol, polypropyleneglycol, (poly)glycerin, 2-butene-1,4-diol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethyleneoxypropylene block copolymers, pentaerythritol, sorbitol, and the like; epoxy compounds such as (poly)ethyleneglycoldiglycidylether, digycerolpolyglycidylether (poly)propyleneglycoldiglycidylether, glycidol, and the like; multivalent amine compounds and condensation products of the multivalent amine compounds and haloepoxy compounds, such as ethylenediamine, diethylenetriamine, triethylenetetramine, tetraethylenepentamine, pentaethylenehexamine, polyamidepolyamine, polyethyleneimine, and the like. multivalent isocyanate compounds such as 2,4-tolylenediisocyanate, hexamethylenediisocyanate, and the like; multivalent oxazoline compounds such as 1,2-ethylenebisoxazoline and the like silane coupling agents such as γ-glycidoxypropyltrimethoxysilane, γ-aminopropyltrimethoxysilane, and the like; alkylene carbonate compounds such as 1,3-dioxolan-2-one, 4-methyl-1,3-dioxolan-2-one 4,5-dimethyl-1,3-dioxolane-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxopan-2-one, and the like; haloepoxy compounds such as epichlorohydrin and the like; hydroxides, chlorides and the like, of zinc, calcium, magnesium, aluminum, iron, zirconium, and the like; and the like.

An amount of the cross-linking agent to use is not particularly limited, but is preferably in a range of from 0.001 mol % to 10 mol %, more preferably in a range of from 0.001 mol % to 1 mol %, and especially preferably in a range of from 0.01 mol % to 0.5 mol %.

In the present invention, there is no particular limit as to how to carry out the polymerization of the monomer constituent. Conventionally well-known polymerization methods such as bulk polymerization, sedimentation polymerization, aqueous solution polymerization, reverse-phased suspension polymerization, and the like may be adopted. Among them, the aqueous solution polymerization is preferable in which an aqueous solution of the monomer constituent is used. The aqueous solution polymerization and the reverse-phased suspension polymerization are preferable. However, the aqueous solution polymerization is especially preferable because the aqueous solution polymerization improves the water-absorbing property of the water-absorbing resin particles, and can be easily controlled.

The reverse-phased suspension polymerization is a polymerization method in which the monomer aqueous solution is suspended in a hydrophobic organic solvent. For example, the reverse-phased suspension polymerization is described in U.S. Pat. Nos. 4,093,776, 4,367,323, 4,446,261, 4,683,274, and 5,244,735, and the like. Moreover, the aqueous solution polymerization is a polymerization method in which the polymerization is carried out with the monomer aqueous solution but without the solvent for dispersion. For example, the aqueous solution polymerization is described in U.S. Pat. Nos. 4,625,001, 4,873,299, 4,286,082, 4,973,632, 4,985,518, 5,124,416, 5,250,640, 5,264,495, 5,145,906, 5,380,808, and the like. The monomers and the polymerization initiators exemplified in the US patents are also applicable to the present invention.

The polymerization reaction may be carried out with stirring the monomer constituent in a kneader, or may be carried out in a stationary manner (without stirring) on a belt or in a box-shaped reactor. Further, the aqueous solution polymerization of the ethylene-based unsaturated monomer may be carried out continuously or batchwisely. Moreover, the aqueous solution polymerization of the ethylene-based unsaturated monomer may be carried out under normal pressure, under reduced pressure, or under pressure. It is preferable that the polymerization reaction be carried out in a stream of an inert gas such as nitrogen, helium, argon, carbon dioxide, or the like, so as to deaerate a monomer component (to preferably attain an dissolved oxygen amount of 1 ppm or lower).

For starting the polymerization reaction, a polymerization initiator, or activation energy rays such as radiation rays, electron rays ultraviolet light rays, electromagnetic rays, and the like. Specific examples of the polymerization initiator are radical polymerization initiators such as: inorganic compounds such as sodium persulfuric acid, ammonium persulfuric acid, potassium persulfuric acid, hydrogen peroxide and the like; organic peroxides such as t-butylhyroperoxide, dibenzoyl peroxide, cumene hydroperoxide, and the like; azo compounds such as 2,2'-azobis(N,N'-methyleneisobutylamidine) and its salts, 2,2'-azobis(2-methylpropyoneamindine) and its salts, 4,4'-azobis-4-cyanovaleirc acid, and the like; and the like.

These polymerization initiators may be used solely, or two or more of them may be used in combination. Moreover, in case a peroxide compound is used as the polymerization initiator, oxidation-reduction (redox) polymerization may be carried out by using, in addition to the peroxide compound, a reductant such as sulfite, bisulfite, L-ascorbic acid, or the like.

In the present invention, it is especially preferable that the hydrate gel-form cross-linked polymer obtained by the polymerization of the monomer constituents have air bubbles inside thereof, because the air bubbles inside improve the water-absorbing property of the resultant water-absorbing resin particles. Such hydrate gel-form cross-linked polymer having the air bubbles inside thereof can be easily obtained by polymerizing, in the presence of the cross-linking agent, the monomer constituent in such a manner that the resultant polymer will have air bubbles inside thereof.

For this polymerization, conventionally well-known methods may be applied, such as a polymerization method in which the polymerization is carried out in the presence of azo-type initiator; a polymerization method in which polymerization is carried out by using carbonate is used as a foaming agent (see Japanese unexamined patent applications, Tokukaihei, publication Nos. 5-237378, and 7-185331, and U.S. Pat. Nos. 5,462,972 and 5,712,316 (the Japanese unexamined patent applications, Tokukaihei, publication Nos. 5-237378, and 7-185331, respectively correspond to U.S. Pat. Nos. 5,154,713, and 5,314,420)); a polymerization method in which a foaming agent (such as pentane, trifluoroethane or the like) that is insoluble in water is dispersed inside the monomer (published U.S. Pat. Nos. 5,328,935 and 5,338, 766); a polymerization method in which a solid particulate-form foaming agent is used (see International publication No. WO96/17884 (which corresponds to U.S. Pat. Nos. 5,985, 944 and 6,251,960); a polymerization method in which the polymerization is carried out in the present of a surfactant under an inert gas atmosphere (see U.S. Pat. Nos. 6,107,358 and 6,455,600).

In case the polymerization of the monomer constituent is carried out in the presence of the cross-linking agent, it is preferable to use water as a solvent. In other words, it is preferable that an aqueous solution of the monomer constituent and the cross-linking agent is used. This is because the use of the aqueous solution improves the water-absorbing property of the water-absorbing resin particles, and allows the foaming agent to perform efficient foaming.

It is more preferable that the aqueous solution (hereinafter referred to as monomer aqueous solution) have a monomer content of generally 15% by weight to 80% by weight, and especially 20% by weight to 60% by weight. If the monomer content was less than 20% by weight, especially 15% by weight, there would be such a risk that the resultant water-absorbing resin particles has a higher water-soluble content. Further the foaming by the foaming agent would be insufficient. In this case, there is a risk that it would become impossible to improve a water absorbing rate. On the other hand, if the monomer content exceeded 60% by weight, especially 80% by weight, it would possibly become difficult to control a reaction temperature and the foaming by the foaming agent.

Moreover, it may be so arranged that a solvent of the monomer aqueous solution is a combination of water and an organic solvent that is soluble with water. Specifically, the organic solvent may be, for example, methyl alcohol, ethyl alcohol, acetone, dimethylsulfoxide, ethyleneglycolmonomethylether, glycerin, (poly)ethylene glycol, (poly)propylene glycol, an alkylene carbonate, or the like. The organic solvents may be used solely or two or more of them may be used in combination. In general, however, the solvent of the monomer aqueous is solely water, or a solvent whose main component is water (for example, water content is 90% by weight to 100% by weight) is used.

The foaming agent to be added in the monomer aqueous solution is a foaming agent that is dispersible or soluble in the monomer aqueous solution. Specifically, the foaming agent may be, for example: volatile organic compounds that is dispersible or soluble in the monomer aqueous solution, such as n-pentane, 2-methylpropane, 2,2-dimethylpropane, hexane, heptane, benzene, substituted benzene, chloromethane, chlorofluoromethane, 1,1,2-trichlorotrifluoromethane, methanol, ethanol, isopropanol, acetone, azodicarbonamide, azobisisobutyronitrile; carbonates such as sodium bicarbonate, ammonium carbonate, ammonium bicarbonate, ammonium nitrite, basic magnesium carbonate, calcium carbonate, and the like; dry ice; acrylic salt of amino group-containing azo compound; and the like. The foaming agents may be used solely or two or more of them may be used in combination.

There is no particular limit as to how much amount of the foaming agent is used with respect to the amount of the monomer. The amount of the foaming agent is used with respect to the amount of the monomer is set arbitrarily depending of which type of foaming agent is used for which type of monomer. However, it is preferable that the amount of the foaming agent be in a range of from 0.001 parts by weight to 10 parts by weight with respect to 100 parts by weight of the monomer. If the amount of the foaming agent exceeded the range, the resultant water-absorbing resin particles would have insufficient water-absorbing property.

The water-absorbing resin particles according to the present invention may be obtained by crushing the hydrate gel-form cross-linked polymer. There is no particular limitation as to how to crush the hydrate gel-form cross-linked polymer. (The crushing may be carried out together with the polymerization (for example, kneader polymerization), or may be performed after the polymerization. Or the crushing may be carried out together with the polymerization and then performed again thereafter.) For example, the hydrate gel-form cross-linked polymer may be crushed (a) by using a meat chopper (see U.S. Pat. No. 5,275,773), (b) by using a crusher having a rotating blade(s) (see U.S. Pat. No. 6,140, 395), (c) by crushing the hydrate gel-form cross-linked polymer that has been frozen in advance (see U.S. Pat. No. 6,100, 305), or (d) the like method. Moreover, examples of the method by which the hydrate gel-form cross-linked polymer is crushed by the crusher having the rotating blade(s), include a method in which the hydrate gel-form cross-linked polymer is crushed by shearing by using a fixed blade and a rotating blade; a method in which the hydrate gel-form cross-linked polymer is cut by a cutting apparatus provided with a pair of rotating blades provided at different axes and rotated overlapping each other at least partially; a method in which the hydrate gel-form cross-linked polymer is cut by using a cutting apparatus with application of a lubricant, the cutting apparatus having a rotating blade.

Moreover, the thus crushed hydrate gel-form cross-linked polymer may be dried/pulverized if necessary, and then shaped into the water-absorbing resin particles. The drying of the thus crushed hydrate gel-form cross-linked polymer may be carried out by a well-known drying method such as hot-air drying, infrared drying, microwave drying, drum-dryer drying, azeotropic dehydration in a hydrophobic organic solvent, or the like method. There is no particular limit as to how to dry the thus crushed hydrate gel-form cross-linked polymer. Moreover, drying condition may be appropriately set so that the water-absorbing resin particles will have a solid content within a desired range, and a moisture content, preferably of 10% by weight or less, more preferably of from 1% by weight to 8% by weight, further preferably of from 2% by weight to 7% by weight. (Note that the moisture content is specified by drying loss after heating the particles for three hours in an oven kept at 180° C.)

Moreover, the thus crushed hydrate gel-form cross-linked polymer may be further pulverized, granulated, or classified, after the drying, so as to adjust the diameter of the resultant water-absorbing resin particles. There is no particular limit as to the weight-average diameter of the water-absorbing resin particles. However, the weight-average diameter of the water-absorbing resin particles is preferably in a range of 100 μm to 800 μm, more preferably in a range of 280 μm to 500 μm, and more preferably in a range of 350 μm to 450 μm.

Moreover, it is preferable that a diameter distribution of the water-absorbing resin particles be narrow. For example in case where the classification is carried out with a sieve of 850 μm mesh and a sieve of 150 μm mesh, the sieve of 850 μm mesh traps 1% by weight or less (lower limit is 0% by weight), preferably 0.5% by weight or less, and more preferably 0.1% by weight or less, of the particles, whereas the sieve of 150 μm passes 10% by weight (lower limit is 0% by weight), preferably 5% by weight, more preferably 3% by weight, and especially preferably 1% by weight, of the particles. By adjusting the diameter to be within the range, it is possible to further improve the water absorbing capacity. Note that the water-absorbing resin particles may have a spherical shape, a scale-like shape, an inconstant as-crushed shape, a particle-like shape (powder form), or other various shapes. Note that the ratio of the trapped particles by the sieve of 850 μm mesh and the passed particles by the sieve of 150 μm is applicable to the later-described particle-shape water-absorbing resin material (final product) of the present invention.

(II) Surface Treatment of Water-Absorbing Resin Particles

By subjecting its surface to secondary cross-linking by using a surface cross-linking agent, it is possible to give the thus obtained water-absorbing resin particles a higher cross-linking density in a vanity of its surface (for example, 10% or less, especially 1% or less of thickness of surface layers of the particles). The water-absorbing resin particles, which are obtained by the present invention, is further improved in terms of liquid permeability, water absorbency, water absorbency against pressure, and liquid permeability against pressure.

The surface cross-linking agent may be any compound as long as the compound have a plurality of reactive groups and is reactive with a functional group, such as a carboxyl group or the like, of the water-absorbing resin particles. A well-known surface cross-linking agent, which is generally used for this purpose, may be adopted. Specific examples of the surface cross-linking agent include, multivalent alcohols such as (poly)ethylene glycol, diethyleneglycol, (poly)propyleneglycol, triethyleneglycol, tetraethyleneglycol, 1,3-propanediol, dipropyleneglycol, 2,2,4-trimethyl-1,3-pentanediol, (poly)glycerin, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropyrene, oxyethylene-oxypropylene block copolymer, pentaerythritol, sorbitol, polyvinylalcohol, glucose, mannitol, sucrose, grape sugar, and the like; multivalent epoxy compounds such as ethyleneglycoldiglycidylether, polyethyleneglocoldiglycidylether, glycerolpolyglycidyletehr, diglycerolpolyglycidylether, polyglycerolpolyglycidylether, (poly)propyleneglycoldiglycidylether, and the like. multivalent amine compounds such as ethylenediamine, diethylenetriamine, triethylenetetramine, tetraethylenepentamine, pentaethylenehexamine, polyethyleneimine and the like; multivalenet isocyanate compounds such as 2,4-tolylenediisocyanate, hexamethylenediisocyanate, and the like; multivalent oxazoline compounds such as 1,2-ethylenebisoxazoline, and the like, and oxazolidinone compounds such as (N-acyl)(bis-)2-oxazolidinone and the like (see U.S. Pat. No. 6,559,239); alkylene carbonate compounds (see U.S. Pat. No. 5,409,771) such as 1,3-dioxolan-2-one, 4-methyl-1,3-dioxolan-2-one, 4,5-dimethyl-1,3-dioxolane-2-one, 4,4-dimethyl-1,3-dioxolan-2-one 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxopan-2-one, and the like; haloepoxy compound such as epichlorohydrin and the like; cyclic urea compounds; oxetane compounds (see published US patent application No. 2002/72471); haloepoxy compounds epichlorohydrin, epibromhydrine, α-methylepichlorohydorin and the like; hydroxides, chlorides and the like, of zinc, calcium, magnesium, aluminum, iron, zirconium, and the like; and the like. However, the present invention is not particularly limited to these surface cross-linking agents. These surface cross-linking agents may be used solely, or two or more of them may be used in combination.

Of these surface cross-linking agents, the present invention is suitably applicable in a reaction system which particles are easily agglomerated in performing surface cross-linking. That is, the present invention is suitably applicable in a reaction system in which, among the these surface cross-linking agents, a dehydration esterification cross-linking agent (especially a multivalent alcohol; an alkylene carbonate compound; an oxazolidinone; cyclic urea compound; an oxetane compound) is used as the surface crossing agent or its solvent. Especially the present invention is suitably applicable in a reaction system in which the multivalent alcohol is used as the surface crossing agent or its solvent. In other words, the present invention solves the problem of larger property deterioration associated with the use of such dehydration esterification surface cross-linking agents than with the use of ionic reactive cross-linking agents (for example, the multivalent metals) or ring-opening reactive cross-linking agent (for example, the epoxy compound).

Note that the cause of the large property deterioration is deduced that, in the use of the dehydration esterification surface cross-linking agents, the water-absorbing resin generally tends to granulate in the surface cross linking, a high temperature necessary for esterification causes the water-absorbing resin to have a low moisture content, that is, to be a hard water absorbing resin having a low moisture content. Such hard water absorbing resin having a low moisture content is susceptible to process-induced damages to break the particles, and the damages on the surface of the particles) after the surface treatment.

There is no particular limit as to how to carry out the treatment of the particles of the water-absorbing resin with the surface cross-linking agent. Specifically, for example, the treatment may be carried out (1) by mixing the water-absorbing resin particles and the surface cross-linking agent together without using a solvent, (2) by adding the surface cross-linking agent into a solution in which the water-absorbing resin particles are dispersed in a hydrophobic solvent such as cyclohexane, pentane, or the like, (3) by directly spraying or dropping, onto the water-absorbing resin particles in a non-dispersing state, a solution or a dispersion liquid in which the surface cross-linking agent is dissolved or dispersed in a hydrophilic solvent, or (4) by the like method.

Among these methods, the method (3) is more preferable for attaining a maximum effect of the present invention. It is preferable that the hydrophilic solvent be water or a mixture of water and a water-soluble organic solvent. The organic solvent may be, for example, a lower alcohol such as methanol, ethanol, isopropanol, or the like, a multivalent alcohol such as propyleneglycol, polyethyleneglycol, or the like, or the like solvent. Because a reaction temperature of 100° C., preferably or 150° C. or more is necessary for reacting the dehydration esterification cross-linking agent such as the multivalent alcohol, oxetane, these compounds that can serve as the dehydration esterification cross-linking agent may be used as a cross-linking agent or as a solvent, or as an agent performing the functions of the cross-linking agent and the solvent, by adjusting the reaction temperature or duration of the reaction.

With respect to the water-absorbing resin particles, the surface cross-linking agent, water, organic solvent are preferably in a quantitative ratio of 0.001 to 10 parts by weight; 0 to 30 parts by weight; 0 to 30 parts by weight, more preferably in a quantitative ratio of 0.01 to 5 parts by weight; 0.1 to 10 parts by weight; 0 to 10 parts by weight, further preferably in a quantitative ratio of 0.05 to 3 parts by weight; 0.2 to 5 parts by weight; 0 to 5 parts by weight. Among those solvents, the present invention is suitably applicable to a reaction system in which the particles are easily agglomerated in performing the surface cross-linking, especially in a system in which the aqueous solution, especially, the aqueous solution whose main component is water (especially the aqueous solution whose water content is 90 to 100% by weight) is used as the solvent.

The water-absorbing resin particles in which the surface cross-linking agent or the solution thereof is mixed in or dispersed, are generally further subjected to heating treatment so as to react with the surface cross-linking agent. The heating treatment is carried out preferably at a temperature in a range of 50° C. to 250° C., more preferably at a temperature in a range of 80° C. to 230° C., and especially preferably at a temperature in a range of 150° C. to 200° C. Further, a reaction time (heating time) of the heating treatment is appropriately set in a range of 1 minute to 180 minutes, preferably in a range of 10 minutes to 120 minutes. Further, if necessary, cooling (forced cooling) of water-absorbing resin particles is performed after the heating, in order to terminate the reaction.

By performing the secondary cross-linking on the water-absorbing resin particles by using the surface cross-linking agent, the water-absorbing resin particles attains a further improved water absorbency against pressure (AAP). Moreover, the secondary cross-linking reduces an amount of a water-soluble component in the particles (water-soluble component is a component that is dissolved into an aqueous liquid when the particles are in contact with the aqueous liquid). There is no particular limit in terms of an amount of the surface cross-linking agent to use, the heating temperature, and the treatment time can be arbitrarily set depending on (i) which type of surface cross-linking agent is used for which type of water-absorbing resin particles, (ii) target degree of surface cross-linking, and (iii) the like condition.

The surface cross-linking gives the water-absorbing resin particles an absorbency against pressure (AAP; specified in Examples; here the pressure is 0.7 psi or 0.3 psi) of 10 g/g or more, preferably of 15 g/g or more, more preferably of 20 g/g or more, further preferably of 22 g/g or more, further more preferably of 24 g/g or more, and especially preferably of 26 g/g or more. Moreover, the surface cross-linking gives the water-absorbing resin particles an absorbency under no pressure (CRC (Centrifuge Retention Capacity); specified in Examples) generally of 20 g/g, preferably of 28 g/g or more, more preferably of 30 g/g or more, further preferably of 32 g/g or more, and especially preferably of 34 g/g or more. The present invention is suitably applicable to water-absorbing resin particles having a high absorbency, and conventionally being susceptible to damages. According the present invention, it is possible to attain a particle-shape water-absorbing resin material that retains the high absorbency even if the additive is added. Note that there is no particular upper limit for the AAP and CRC. However, there is a case where the AAP and CRC of about 80 g/g, or even about 70 g/g are considered to be sufficient in consideration of a balance between with manufacturing cost. Moreover, the surface cross-linking gives the water-absorbing resin particles a liquid permeability, for example, Saline Flow Conductivity (SFC; specified in published US patent application, No. US2004-0106745-A) preferably of 1 (unit: $\times 10^{-7}$ cm$^3$ s/g) or more, more preferably of 10 or more, further preferably of 20 or more, especially preferably of 40 or more, and more especially preferably 80 or more.

Note that in the present invention it may be so arranged that water is added to the water-absorbing resin particles after the surface treatment, in order to adjust the moisture content of the particles. In this case, an amount of water to added is less than 5%. Moreover, in order to adjust the moisture content of the particles of water-absorbing particles, an aqueous solution of a water-soluble compound (in an amount of 0 to 10% by weight in general) may be added to the water-absorbing resin particles after the surface treatment. The water-soluble compound may be, for example: a metal salt such as aluminum sulfate, alum, common salt, sodium hydrogensulfite, sodium phosphate, or the like; an antioxidant; a deodorant such as dry distillation product or extract, of tea leaves or the like deodorant; an antibacterial agent; a preservative; an aromatic substance; a chelating agent; a surfactant; or the like.

(III) Agglomerated Particles

The water-absorbing resin particles according to the present invention are produced as described above. Note that, in the method in which the surface treatment of the water-absorbing resin particles is carried out by using the hydrophilic solvent, the hydrophilic solvent is generally evaporated off by heating the particles during or after the surface treatment. By doing this, it is possible to dry the water-absorbing resin particles.

However, in evaporating off the hydrophilic solvent, especially in evaporating off water, there is a possibility that the water-absorbing resin particles would be agglomerated together into agglomerated particles. It is surmised that water having been moved to the surface in evaporating off the water, acts as a plasticizer and thus facilitates the water-absorbing resin particles to be agglomerated with each other. The more amount of water-absorbing resin particles are agglomerated in the case where the dehydration reaction cross-linking agent, especially, the multivalent alcohol, is used, and in case where water is used as a main component of the solvent. The present invention is suitably applicable to those cases, especially in case where the aqueous solution of the multivalent alcohol is used for the surface cross-linking.

In general, in case where the agglomerated particles have a diameter greater than 1 mm, more specifically 850 μm, which is a size to be filtered out by the JIS standard sieve, the particles will not be suitable for use in a sanitary material such as a diaper and the like. This is because the sanitary material in which the agglomerated particle having such diameter is used gives stiff and rough feeling to users when wearing it, and because the agglomerated particle having such diameter sometimes break through a top sheet of the diaper. For this reason, it is necessary to perform the particle-size regulating treatment so as to the water-absorbing resin particles so as to break apart the particles including the agglomerated particles into individual particles. Further, in order to attain high-quality water-absorbing resin particles, it is preferable to add an additive to the water-absorbing resin particles, wherein the additive may be of various kinds to give the particle various function.

In the following, the step of performing the surface treatment (in other words, surface cross-linking) of the water-absorbing resin particles is referred to as a surface treatment step (A) (step (A)), the step of performing the particle-size regulating treatment of the water-absorbing resin particles is referred to as a particle-size regulating step (B) (Step (B)), and the step of adding the additive is referred to as a adding step (C) (step (C)). Further, the step of mixing the additive and the water-absorbing resin particles is referred to as a mixing step (D) (step (D)).

(IV) Particle-Shape Water-Absorbing Resin Material

The method of present invention for producing the particle-shape water-absorbing resin material is so arranged that, the adding step (C) and the mixing step (D) are performed in the particle-size regulating step (B), where the particle-size regulating step (B) is of (pulverizing and/or classifying) performing the particle size regulation of the surface-treated water-absorbing resin particles (including the agglomerated particles among them), and preferably pulverizing the agglomerated particles (agglomerated particles due to the surface cross-linking) of a certain size or larger, the adding step (C) is of adding the additive, the mixing step (D) is of uniformly mixing the additive and the water-absorbing resin particles, and the additive is for giving a function of various kinds to the water-absorbing resin particles. With this arrangement, it is possible to obtain a particle-shape water-absorbing resin material having the function without deteriorating its property.

Hereinafter, the particle-size regulating step (B) and the step of mixing will be described in detail.

As to a particle-size regulating apparatus for use in the particle-size regulating step (B), there is no particular limit, provided that the particle-size regulating apparatus is capable of pulverizing and/or classifying the agglomerated particles. In the present embodiment, a rotary particle-size regulating apparatus or a rotary continuous size particle controlling apparatus is preferably used. An example of the rotary particle-size regulating apparatus is a knife cutter rotary particle-size regulating apparatus having a function of pulverizing and/or classifying. Specific examples of the rotary particle-size regulating apparatus include: New Speed Mil (Product Name: made by Okada Seiko Co., Ltd.), Flush mil (Product Name: made by Fuji Paudal Co., Ltd.), Speed Mill (Product Name: made by Showa Engineering Co., Ltd.) and the like. Note, the rotary particle-size regulating apparatus performs the pulverizing by using a rotating blade, such as a knife cutter, of the particle-size regulating apparatus, and the classification by using a grate, a net, a punching metal, or the like, of the particle-size regulating apparatus. The particles having been pulverized/classified to have a certain diameter or less are continuously discharged from the apparatus.

Specifically, the rotary particle-size regulating apparatus has the rotating blade. By rotating the rotating blade at a high speed, a mechanical force is given to the water-absorbing resin particles, thereby breaking apart the agglomerated water-absorbing resin particles into the individual particles (primary particles). Moreover, the rotary particle-size regulating apparatus is provided with an inlet and an outlet. In the particle-size regulating step (B) according to the present invention, the particles, including the agglomerated water-absorbing resin particles are continuously introduced gradually via the inlet in order to perform continuous particle-size regulating treatment. After the particle-size regulating treatment, the resultant water-absorbing resin particles are discharged via the outlet. Note that the discharge of the water-absorbing resin particles after the particle-size regulating treatment becomes more efficient if the discharge is carried out while sucking out the particles by using a blower (rotating fan) or the like.

In general, the rotating blade of the rotary particle-size regulating apparatus in the particle-size regulating step (B) is rotated at a rotation speed in a range of 50 rpm to 5000 rpm. It is preferable that the rotating blade of the rotary particle-size regulating apparatus in the particle-size regulating step (B) is rotated at a rotation rate preferably in a range of 100 rpm to 1000 rpm, and more preferably in a range of 300 rpm to 700 rpm. If the rotation speed was less than 100 rpm, especially less than 50 rpm, the rotation speed of the rotating blade of the rotary particles size regulating apparatus would be too slow to perform the particle-size regulating treatment of the surface-treated water-absorbing resin particles and the agglomerate particles thereof. Thus, the rotation of the rotating blade would merely cause the mixing of the particles and the agglomerated particles. Therefore, the rotation speed of less than 100 rpm is not preferable. Whereas, if the rotation speed was more than 1000 rpm especially 5000 rpm, the rotation speed would be so excessively fast that the excess impact would be given to the water-absorbing resin particles, thus resulting in production of a large amount of smaller particles (particulates) of water-absorbing resin.

Moreover, for the most effective application of the present invention, it is preferable to apply the present invention in a large-scale continuous production in which a large damage is given to the particles. The large-scale production has a production amount, per production line (apparatus), of 50 kg or more per hour preferably, 100 kg or more per hour more preferably, 500 kg or more per hour especially preferably, and 1 ton or more per hour more especially preferably. Note that there is no particular limit as to an upper limit of the production scale, but the production scale is about 100 metric ton in general.

In the particle-size regulating step (B) and the mixing step (D), it is preferable that the water-absorbing resin particles has a temperature higher than room temperatures. The temperature of the water-absorbing resin particles is regulated to be preferably in a range of 35° C. to 100° C., more preferably in a range of 40° C. to 95° C., and especially preferably in a range of 45° C. to 90° C., when the additive is added and mixed with the particles. As for how to control the temperature of the water-absorbing resin particles within the temperature range, heating and the temperature of the particles are increased by heating and keeping the temperature appropriately. Moreover, the temperature is controlled within the temperature range by appropriately cooling and keeping the temperature after the heat treatment in the surface cross linking treatment. If the water-absorbing resin particles had a low material temperature, it would possibly result in non-uniform mixing, or the particle agglomeration. Moreover, if the heat treatment in the surface cross linking treatment. A high material temperature of the water-absorbing resin particles causes deterioration or staining of the water-absorbing resin particles and is disadvantageous in terms of energy consumption.

By the particle-size regulating step (B), the agglomerated water-absorbing resin particles are broken apart from each other, thereby converting into the primary water-absorbing resin particles as it has been before, or particles having a predetermined diameter, for example, such a diameter that allows the particles to pass through a sieve of 8501 μm to 600 μm mesh.

Moreover, as described as above, the first method of the present invention for producing the particle-shape water-absorbing resin material is so arranged that the mixing step (D) is performed in the particle-size regulating step (B). Here, the wording the "mixing step (D) is performed in the particle-size regulating step (B)" indicates that the mixing step (D) is carried out during the particle-size regulating step (B). So, the mixing step (D), and the particle-size regulating step (B) are performed together. That is, the step (B) and step (D) are performed in one operation, so as to add the additive for giving a function to the water-absorbing resin particles, and to mix the additive and the particle in performing the particle-size regulating treatment by using the rotary particle-size regulating apparatus. With this arrangement, it is possible to concurrently perform the particle-size regulating treatment for the agglomerated water-absorbing resin particles, and mixing of the additive, and the water-absorbing resin particles. In this arrangement, the particle-size regulating treatment "mixes" the particles and the additives. Thus, the particle-size regulating treatment plays the role of steps (B) and (D) for the particle-size regulating treatment and the mixing. Therefore, it becomes possible to reduce the damage onto the surfaces of the water-absorbing resin particles. Thus, it is possible to obtain a particle-shape water-absorbing resin material having various functions without deteriorating its property.

The additive is added at any time from beginning to end of the particle-size regulating treatment of the water-absorbing resin particles. The additive may be added to the water-absorbing resin particles that have been subjected to the surface treatment. Furthermore, the additive may be added as the particle-size regulating treatment is being performed. Moreover, the additive may be added to the particles, including the agglomerated water-absorbing resin particles that are to be again subjected to particle-size regulating step (B), after being subjected to later-described classification. The mixing step (D) is performed in particle-size regulating step (B). However, it is preferable that the mixing is performed before the agglomerated particles are substantially or mostly converted into the primary particles by the rotary particle-size regulating apparatus. With this arrangement, it is possible to shorten time necessary for the particle-size regulating treatment and the mixing. Therefore, it is possible to obtain the particle-shape water-absorbing resin material efficiently. Moreover, this shortening of time shortens a time during which the surfaces of the water-absorbing resin particles are damaged. Because of this, it becomes possible to further reduce the damage onto the surfaces of the water-absorbing resin particles.

Moreover, the second method of the present invention of producing the particle-shape water-absorbing resin is so arranged that the particle-size regulating step (B) and the mixing step (D) are performed within 10 minutes in total. It is preferable to arrange the second method such that the particle-size regulating step (B) and the mixing step (D) are performed together as in the first method in which the particle-size regulating step (B) and the mixing step (D) are performed together. However, the particle-size regulating step (B) and the mixing step (D) may be performed separately but within 10 minutes in total.

According to the first and the second methods of the present invention, the particle-size regulating step (B) and the mixing step (D) may be performed together or separately (in case of the second method), and the time for the particle-size regulating treatment and the mixing is, in total, preferably 10 minutes or shorter (generally in a range of 0.01 second to 10 minutes), more preferably in a range of 0.1 second to 5 minutes, further preferably in a range of 0.5 second to 3 minutes, especially preferably in a range of 1 second to 1 minutes, and most preferably in a range of 1 to 30 seconds. If the time was excessively short, the mixing and the particle-size regulating treatment would become insufficient in general. Moreover, if the time was excessively long, it would result in a particle-shape water-absorbing resin material having a deteriorated property due to the damage given to the surfaces of the particles. In the conventional method, it was found that the mixing of the particles and the additive, and the pulverizing of the agglomerated particles cause damage on the surface of the resultant particles thereby deteriorating the property of the particle-shape water-absorbing resin material. However, in the present invention, the uniform mixing is attained in a much shorter time than the conventional art, and thus it is possible to obtain a particle-shape water-absorbing resin material having a high property. In order to attain such a short time, for example the mixing and the particle-size regulating treatment are performed together, thereby carrying out continuous mixing and continuous particle-size regulating treatment.

Specifically, the particle-size regulating treatment and the mixing of the particles and the additive, which conventionally take several ten minutes to several hours, are carried out instantly according to the present invention. Conventionally, it is considered that a high property is attained by long-time mixing to uniformly mix the particles and the additive. However, the inventors of the present invention found out that such long-time mixing is actually the cause of the deterioration of the properties, especially, liquid permeability, of the particles.

The present invention is accomplished based on this finding. It was found out that the property deterioration due to the long-time mixing is severe when the additive is powder form, especially, water insoluble inorganic powder. The long-term mixing causes more severe property deterioration if the particles (for example, silica particulates) are agglomerated. It is suitably applicable in the present invention.

Even though the first method of the present invention is arranged such that the particle-size regulating step (B) and the mixing step (D) are performed together, the second step may be arranged such that the particle-size regulating step (B) and the mixing step (D) are performed together or separately, as long as the particle-size regulating step (B) and the mixing step (D) are performed within 10 minutes in total. However, it is preferable to arrange the second method that the particle-size regulating step (B) and the mixing step (D) are performed together. In case the second method is arranged as such, it is possible to adopt the similar arrangement to that of the first method.

In case where the second method is arranged such that the steps (B) and (D) are performed separately, the mixing step (D) is performed by using an ordinary mixing apparatus and much shorter-time mixing than the conventional mixing (the steps (B) and (D) are performed within 10 minutes in total) is performed. The mixing apparatus used in the second method may be an air-flow type mixing apparatus or a rotation stirring type mixing apparatus (these apparatuses are continuous type or batch type). Especially, the rotation stirring mixing apparatus is preferable. Examples of the mixing apparatus include mechanical mixing apparatuses such as a conical blender, a nauta mixer, a kneader, a V-shape mixing apparatus, a flow type mixing apparatus, a turbulizer, a Lödge mixer, a screw mixer, a ribbon mixer, a mortar mixer, and the like. The rotating stirring type mixing apparatuses perform with rotation rate generally in a range of 10 rpm to 1000 rpm, especially in a range of 100 rpm to 5000 rpm.

Moreover, the inventors of the present invention found out that signification property deterioration is caused after the surface cross-linking treatment in the production of the particle-shape water-absorbing resin material, and the particle-size regulating treatment and the mixing accounted for the property deterioration, thereby accomplishing the present invention. Therefore, regardless of the types of the apparatuses, the time for the particle-size regulating treatment and the mixing is important, and is regulated within the range in the present invention. The time is easily measured or calculated from retention time to dwell in the apparatuses (for mixing and for particle-size regulation) and transportation time to be transferred therebetween.

Conventionally, it was demonstrated that the particle-shape water-absorbing resin material cannot have a high property in a large-scale production, even though it can have a relatively high property in a small-scale production, such as, a laboratory-scale production. The studies for the cause of the property deterioration in the large-scale production found out that the property is significantly deteriorated in the particle-size regulating treatment and the mixing. The present invention solves this conventional problem by controlling each of the particle-size regulating treatment and the mixing, and the duration of time to carry out them.

For the most effective application of the present invention, it is preferable that the steps (A) to (D) be performed substantially continuously with a conveying step interposed therebetween. Another step (such as the step of granulating) may be provided between the steps. It is preferable that the step B of the particle-size regulating treatment follows the step A of performing the surface treatment. What the wording "the step B of the particle-size regulating treatment follows the step A of performing the surface treatment" indicates is that the step of conveying or the step of storing may be provided between the steps (A) and (B), but the steps (A) and (B) are substantially continuous via the step of conveying.

(V) Additive

The additive, being capable of giving a function of various kinds to the water-absorbing resin particles, is preferably in the powder form at normal temperatures. Inorganic powder, organic powder, other water-absorbing resin particles, or the like may be used as the additive. However, a liquid compound may be used as the additive. Further, a solution or a dispersion liquid of the additive may be added. The additive may be added in a gas state. Note that it may be arbitrarily selected whether the additive is water soluble or water insoluble.

The function to give to the particles may be, for example, flowability (anti-blocking (anti-caking) property), stability against deterioration with age, deodorization/antibacterial property, shock resistance, hydrophilic property/absorption rate, color (or anti-coloring), etc. By adding and mixing the additive into the particles, these functions may be given to the particles, or in case where the particles have already had the functions, it is possible to further improve the function. The additive gives the function to the particles by existing on the surface of the particles.

Specific examples of the inorganic powder include: sulfur-containing inorganic compounds such as sodium sulfite, sodium hydrogensufite, and the like (see U.S. Pat. No. 4,863,989); phosphorous-containing inorganic compounds such as phosphate salt, and the like; apatite, activated carbon, alumina, silica, zeolite, zirconia, bentonite, cement, silica particulates, kaolin, talc, clay, diatomite, sodium carbonate, calcium carbonate, magnesium carbonate, sodium sulfate, aluminum sulfate, alum, calcium oxide, magnesium oxide, zinc oxide, titanium oxide, zinc sulfide, and their complex oxides (for example, complex silicic salt), and the like.

Moreover, specific examples of the organic powder include: metallic soaps such as stearic salts and the like; surfactants such as polyoxyethylenealkylethers, sorbitan fatty acid ester and the like; water-soluble polymers such as polyethyleneoxide, polyacrylic acid, polyacrylic acid soda, polyvinylpyrrolidone and the like; polyethylene; cellulose powder; organic acid (salt) such as L-ascorbic acid (salt), nitric acid (salt), succinic acid (salt) and the like; radical inhibitors (see U.S. Pat. No. 4,972,019) such as hydroquinone, methoquinone, and the like; chelating agents (see U.S. Pat. No. 6,599,989) such as ethylenediamine tetracetic acid (salt), diethylenepentaaminepentacetic acid (salt), ethylenediaminedisuccinic acid (salt) and the like; cyclodextrin; powder of plant origin, such as tea leaf powder, powder of bamboo, sawdust of Japanese cypress, and the like; and the like.

Examples of the liquid compound are liquid compounds that are in the liquid state at normal temperature. Specific examples of the liquid compounds include: surfactants such as sorbitan monostearate and the like; polyols such as propyleneglycol, (poly)ethyleneglycol, and the like; monools such as methoxy(poly)ethyleneglycol and the like; and the like.

Those solid or liquid compounds, as they are, may be added to the water-absorbing resin particles, or a solution or a dispersion liquid thereof may be added to the particles. Further, the solid or liquid compounds may be appropriately vaporized so as to add a gas thereof to the particles. Note that it is preferable to use water or an aqueous solution as a solvent in the case where the solution or the dispersion liquid thereof is used. In this case, an amount of the solvent is preferably in a range of 0 part to 50 parts by weight, more preferably in a range of 0.1 parts to 30 parts by weight, and further preferably in a range of 0.5 parts to 10 parts by weight, with respect to 100 parts by weight of the water-absorbing resin particles.

For most effective use of the present invention powders, especially the inorganic powders and organic powders are preferable among the additives. The water-insoluble powders are more preferable, and water-insoluble organic powders are especially preferable. The powder may be added, in a slurry form, by wet blending. However, it is preferably to add the additive in the powder form to the particles in the powder form, that is, by dry blending, for the sake of the most effective use of the present invention. A diameter of the powder as the additive is preferably in a range of 0.001 μm to 500 μm, more preferably in a range of 0.005 μm to 1100 μm, and especially preferably in a range of 0.01 μm to 10 μm.

Moreover, the property deterioration due to the mixing time, which the present invention is first to notice, is severe in case of powder. The agglomerated powder, especially, the agglomerated inorganic powder show the sever property deterioration due to the mixing time. Moreover, it is found that the permeability is remarkably deteriorated among the properties deteriorated due to the mixing time. Typical examples of the agglomerated powder include: silica particulates such as Aeroil (made by Degussa AG), Tokuseal and Reoloseal (made by Tokuso Co. Ltd.), Canplex (made by Shionogi & Co., Ltd.), and the like; alumina particulates; titania particulates; and the like. These particulates are inorganic powders having a primary diameter of generally 1 nm to 1000 nm, and preferably 10 nm to 100 nm, and being agglomerated to have a diameter 10 to 1000 times larger than the primary diameter. That is, the producing method, especially the second method, of the present invention is preferably applicable to the case where the additive to the water-absorbing resin particles are agglomerated powder. The use of the method, especially the second method gives the particle-shape water-absorbing resin material having a much higher permeability or anti-blocking than the conventional particle-shape water-absorbing resin material.

It is surmised that not only the water-absorbing resin particles but also the additive is damaged in the mixing in the conventional method in which the long-time mixing is performed. The damage on the additive (destruction of the additive, falling-off of the additive, etc.) is also a cause of the property deterioration.

The other water-absorbing resin particles are water-absorbing resin particles that are different from the water-absorbing resin particles used in the present invention. It is possible to give the function to the water-absorbing resin particles of the present invention, by adding the other water-absorbing resin particles to the water-absorbing resin particles of the present invention. Moreover, it is preferable that the other water-absorbing resin particles have a property or shape different from that of the water-absorbing resin particles of the present invention. For example, it may be so arranged that different types of water-absorbing resin particles having different polymer compositions, properties, and/or diameter distributions. Further, it may be so arranged that water-absorbing resin particles having an irregular-broken shape, which are obtained by the aqueous solution polymerization, are mixed with water-absorbing resin particles having a spherical shape, which are obtained by the reverse-phase suspension polymerization. By using, in combination, different types of the water-absorbing resin particles having different properties and shapes, it is possible to control bulk density, permeability, and gel blocking, which are difficult to control with the arrangement in which a sole type of the water-absorbing resin particles is used. Moreover, an amount of the additive to added depends on the type of the additive and the purpose of the addition of the additive. However, the amount of the additive to add is preferably in a range of 0.0001 parts to 100 parts by weight, more preferably in a range of 0.01 parts to 10 parts by weight, and especially preferably in a range of 0.1 parts to 3 parts by weight, with respect to 100 parts by weight of the water-absorbing resin particles. If the amount of the additive to added was less than 0.0001 parts by weight with respect to 100 parts by weight of the water-absorbing resin particles, the effect of the additive could not be attained. If the amount was more than 100 parts by weight, it would become difficult to uniformly mix the additive into the particles. Therefore, the amounts of the additive out of the range are not preferable.

Note that the additive may or may not be crushed or pulverized by using the particle-size regulating apparatus, in mixing the additive and the water-absorbing resin particles in the mixing step (D). It is possible to give the function to the particles without crushing or pulverizing the additive. However, in the case where the additive is crushed or pulverized, the additive will be finer particles. The finer additive is easy to be mixed with the water-absorbing resin particles, and gives the function to the particles more efficiently. (Note that the crushing is an operation to break apart the agglomerated particles.)

By the mixing step (D), it is possible to uniformly mix the additive and the water-absorbing resin particles. By performing the mixing step (D) in the particle-size regulating step (B) especially according to the first method, it is possible to produce the particle-shape water-absorbing resin material of the present invention. By performing the mixing step (D) and the particle-size regulating step (B) within 10 minutes in total according to the second method, it is possible to produce the particle-shape water-absorbing resin material of the present invention.

There is a case where it is difficult to crush the agglomerated particles among the water-absorbing resin particles. In this case, the agglomerated particles, which have survived the particle-size regulating treatment, remain among the water-absorbing resin particles.

The weight-average diameter (specified in JIS standard sieve classification) of the particle-shape water-absorbing resin material having been subjected to the particle-size regulating treatment is in a range of 100 μm to 800 μm. However, to be used in practice, the particle-shape water-absorbing resin material is preferably in a range of 250 μm to 600 μm, more preferably in a range of 280 μm to 500 μm, and especially preferably in a range of 350 μm to 450 μm.

For this reason, it is preferable to subject the particle-shape water-absorbing resin material to the classification after the particle-size regulating step (B). The classification is so carried out as to attain the preferable weight-average diameter. For example, it is preferable to carry out the classification with an adequate sieve of a mesh of 850 μm to 600 μm. In the following the step of performing the classification is referred to as the classification step (E).

By the classification step (E), the agglomerated particles that have survived the particle-size regulating treatment, are separated off and reintroduced into the rotary particle-size regulating apparatus. By doing this, it is possible to break apart/classify all the agglomerated particles remained in the particle-shape water-absorbing resin material. Moreover, by the classification step (E), it is possible to separate off, from the particle-shape water-absorbing resin material, the agglomerated particles that have not passed through the an adequate sieve of a mesh of, for example, 850 μm to 600 μm. The thus separated-off agglomerated particles are reintroduced into the rotary particle-size regulating apparatus via a transportation means such as a bucket conveyer, flight conveyer, a screw conveyer, pneumatic transportation or the like. In the present invention, it may be arranged so that the additive is added to the agglomerated particles that are thus separated off in the classification, and then the agglomerated particles and the additive are reintroduced into the rotary particle-size regulating apparatus. Moreover, it is possible to separate off the particles of smaller diameters from the particle-shape water-absorbing resin material by using an adequate sieve of, for example, 450 μm to 425 μm mesh, or 100 μm to 300 μm mesh, in addition to the sieve of 850 μm to 600 μm mesh. As a result, it is possible to obtain a particle-shape water-absorbing product having a narrow diameter distribution. As the means to separate off the particles of a smaller diameter from the particle-shape water-absorbing resin material, it is possible to use well-known classification means such as air classification, apart from the sieve classification.

Moreover, it is possible to prolong retention time of the particle-shape water-absorbing resin composition by providing the classification step (E) in addition to the particle-size regulating step (B) and the mixing step (D). Specifically speaking, the water-absorbing resin particles and the additive are also stirred and mixed in the classification step (E). This gives a longer mixing time to the water-absorbing resin particles and the additive. As a result, it is possible to attain a particle-shape water-absorbing resin material production in which the additive is uniformly mixed. The classification step (E) of the present invention may adopt, for example, the sieve classification or the air flow classification, preferably the sieve classification (especially sieve vibrating classification).

The weight-average diameter s of the water-absorbing resin particles and the particle-shape water-absorbing resin material can be measured in the following method: the weight-average diameter s of the water-absorbing resin particles or the particle-shape water-absorbing resin material is sieved by using JIS standard sieves (of mesh sizes of 850 μm, 7101 μm, 6001 μm, 500 μm, 425 μm, 300 μm, 2121 μm, 150 μm, 45 μm, and the like). Residual percentage R is plotted on a logarithmic probability paper. The diameter corresponding to R=50% by weight is considered as the weight-average diameter (D50). By this, it is possible to obtain the weight-average diameter (D50). Moreover, the sieving carried out in the measurement of the weight-average diameter (D50) is carried out as follow: for example, 10.0 g of the water-absorbing resin particles or the particle-shape water-absorbing resin material is added into the JIS standard sieves Z8801 (of mesh sizes of 850 μm, 710 μm, 600 μm, 500 μm, 425 μm, 300 μm, 212 μm, 150 μm, 45 μm, and the like: product name: The Iida Testing Sieve; 8 cm in diameter). Then, the water-absorbing resin particles or the particle-shape water-absorbing resin material in the sieves are sieved for 5 minutes by using a shaking classification apparatus (Product Name: Iida Sieve Shaker, Type: ES-65. Ser. No. 0501).

Next, the producing method of the particle-shape water-absorbing resin material is explained below referring to FIG. 1. FIG. 1 is a flow chart schematically showing the producing method of the particle-shape water-absorbing resin material of the present invention. As shown in FIG. 1, the additive is added to the surface-treated particles (WARP in FIG. 1), which include the agglomerated water-absorbing resin particles (agglomerations in FIG. 1) (adding step a). The additive and the particles including the agglomerated particles are introduced into a particle-size regulating apparatus (rotary particle-size regulating apparatus; PSR apparatus in FIG. 1). Then, the particle-size regulating step (B) (PSR step in FIG. 1) and the mixing step (D) are performed together (concurrently). After that, the classification step (E) is performed. The classification step separates the particles into (i) the non-regulated water-absorbing resin particles (non-regulated WARP in FIG. 1) (which the particle-size regulating treatment failed to regulate their particle size), and (ii) the regulated particle-shape water-absorbing resin material (whose particle size is regulated by the particle-size regulating treatment successfully; regulated PSWARM in FIG. 1). The particle-shape water-absorbing resin material is further processed to be a final product. The non-regulated particles, including the agglomerated water-absorbing resin particles are reintroduced (fed back) into the particle-size regulating apparatus. In the case where the additive is added in the adding step a, the additive may be added again (adding step b) when reintroducing the particles, which include the agglomerated water-absorbing resin particles. By doing this, the mixing step (D) is carried out in the particle-size regulating step (B), and all the particles, which include the agglomerated particles, are granulated/classified.

Moreover, the addition of the additive may be carried out at a timing other than in the adding step a (or adding step b). In this case, the particles, which have been surface-treated in the surface treatment step (A) and include the agglomerated particles, are introduced into the particle-size regulating apparatus, and then the additive is added into the apparatus (adding step c).

After that, the particle-size regulating step (B) and the mixing step (D) are performed together (concurrently). After that, the classification step (E) is performed. As in the above case, the particle-shape water-absorbing resin material is further processed to be a final product. The non-regulated particles, including the agglomerated water-absorbing resin particles, are reintroduced into the particle-size regulating apparatus.

Note that in this case, the addition of the additive is carried out separately from the introduction (and reintroduction) of the particles, which include the agglomerated water-absorbing resin particles. Thus, there is no need of adding the additive in the reintroduction. By doing this, the mixing step (D) is carried out in the particle-size regulating step (B), and all the particles, which include the agglomerated particles, are granulated/classified. The particle-shape water-absorbing resin material thus obtained by the method may be further mixed (additional mixing) by using a mixing apparatus. In case of a producing method having no classification step (E), the resultant particle-shape water-absorbing resin material can have a sufficient mixing time by this additional mixing, whereby it is possible to uniformly mix (disperse) the particle-shape water-absorbing resin material whose particles having different diameters. Moreover, in the case of the producing method having the classification step (E), the resultant particle-shape water-absorbing resin material have the weight-average diameter that is regulated to be within a certain range. However, the additional mixing causes the resultant particle-shape water-absorbing resin material to be more uniformly mixed (dispersed). The mixing (and the additional mixing) causes the additive to exist or locally exist on the surface of the water-absorbing resin particles. Therefore, it is possible to efficiently give the function to the water-absorbing resin particles, even if the amount of the additive to add is small.

There is no particular limit in terms of the mixing apparatus for mixing (additional mixing) the particle-shape water-absorbing resin material. For example, a stationary mixing apparatus may be used. The stationary mixing apparatus is an apparatus provided with a housing and a mixing element, and having no driving portion (moving portion). The mixing element is, for example, a combination of a right element and a left element, the right element being a rectangular plate twisted rightward by 180°, and being arbitrarily assembled with the left element being a rectangular plate twisted leftward by 180°. For example, the mixing element is a combination of the right and left element assembled linearly in engagement with each other.

By simply passing the particle-shape water-absorbing resin material through the stationary mixing apparatus, the particle-shape water-absorbing resin can obtain uniformity and homogeneity, by the dividing effect, direction-converting effect, reverting effect, and the like. Moreover, the use of such mixing apparatus having no moving portion do not perform the mechanical mixing. Because of this, the mixing can be performed without making much damage to the particle-shape water-absorbing resin material.

The particle-shape water-absorbing resin material thus mixing uniformly by the stationary mixing apparatus is conveyed to a product hopper and then packed into a bag or the like, so as to be a final product.

The surface cross-linking can give the thus obtained particle-shape water-absorbing resin material an ability of keeping its property. For example, the surface cross-linking gives such high AAP of 10 g/g or more, preferably 15 g/g or more, more preferably 20 g/g or more, further preferably 22 g/g or more, further more preferably 24 g/g or more, and especially preferably 26 g/g or more.

Moreover, the surface cross-linking gives such high CRC of generally 20 g/g or more, preferably 28 g/g or more, more preferably 30 g/g or more, further preferably 32 g/g or more, and especially preferably 34 g/g or more. Upper limits of AAP and CRC may be about 80 g/g for the same reason as above. Moreover, the surface cross-linking gives such SFC of normally 1 (unit; $\times 10^{-7}$ cm$^3$ s/g) or more, preferably 3 or more, more preferably 10 or more, further preferably 20 or more, and especially preferably 40 or more, more especially preferably 80 or more.

Moreover, the weight-average diameter of the thus obtained particle-shape water-absorbing resin material is as described above (it is preferably 250 µm to 600 µm, and more preferably 280 µm to 500 µm). The ratio of the particles trapped by the sieve of 850 µm mesh is preferably 1% or less by weight (lower limit is 0% by weight), more preferably 0.5% or less by weight, and especially preferably 0.1% or less by weight. Moreover, the ratio of the particles passing through the sieve of 150 µm mesh is preferably 10% or less by weight (lower limit is 0% by weight), more preferably 5% or less by weight, further preferably 3% or less by weight, and especially preferably 1% or less by weight. The aforementioned particle size of the particle-shape water-absorbing resin material is attained by appropriately controlling the particle-size regulating treatment (granulation and/classification).

The thus obtained particle-shape water-absorbing resin material has a higher property than a conventional one, even if a smaller amount of additive is added. Further, the thus obtained particle-shape water-absorbing resin material is applicable in various usage of the water-absorbing resin particles. For example, the thus obtained particle-shape water-absorbing resin material may be used in combination with a textile material so as to be suitably used as a body-fluid absorbing product such as disposal diaper and the like.

The following will explain the present invention in more detail with reference to Examples and Comparative Examples, but the present invention is not limited to the Examples described herein. The particle-shape water-absorbing resin material (water-absorbing resin particles in case where the amount of the additive is very little) was measured for absorbency without pressure (CRC), absorbency against pressure (AAP), and saline flow conductivity (SFC).

(Absorbency without Pressure (CRC) of Particle-Shape Water-Absorbing Resin Material)

0.200 g (Wp1) of the particle-shape water-absorbing resin material (or water-absorbing resin particles) was uniformly put into a pouch (60 mm×60 mm; raw material of the pouch is equivalent to EDNA (European Disposables and Nonwovens Association) made of nonwoven fabric. After heat-sealed, the pouch was immersed in a physiological saline (Composition: an aqueous solution of sodium chloride of 0.9% by weight) at a temperature of 23° C. The pouch was taken out of the physiological saline solution 30 minutes later, and was centrifuged for 3 minutes at 250G by a centrifugal separator. After that, weight Wa (g) of the pouch was measured. In addition, the same process was carried out with a pouch (empty pouch) containing no particle-shape water-absorbing resin material (or no water-absorbing resin particles) therein, and weight Wb (g) of the pouch was measured. Then, the absorbency without pressure (g/g) of the particle-shape water-absorbing resin material was calculated by a following formula using Wa and Wb:

Absorbency Without Pressure $(CRC)$ $(g/g) = (Wa(g) - Wb(g) - Wp1(g)$ of particle-shape water-absorbing resin material$)/Wp1(g)$ of particle-shape water-absorbing resin material$)-1$

[Absorbency Against Pressure (AAP) of Particle-Shape Water-Absorbing Resin Material]

To begin with, a measuring apparatus for measuring Absorbency Against Pressure (AAP) of the particle-shape water-absorbing resin material (or water-absorbing resin particles) is briefly explained below, referring to FIG. 2.

Figure 2:
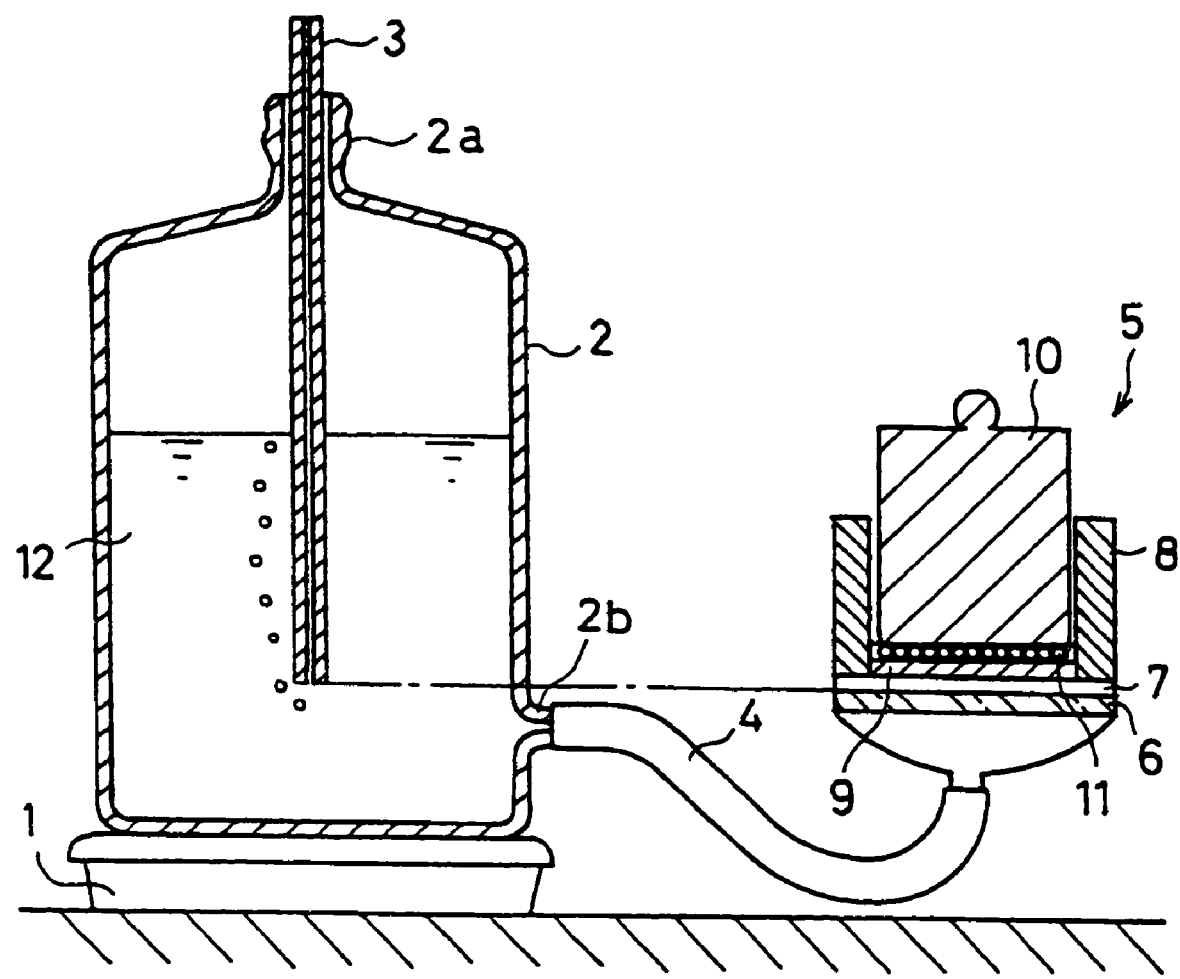
FIG. 2 is a cross-sectional view schematically showing an arrangement of a measurement apparatus for measuring an absorbency against pressure, the measurement apparatus used in Examples of the present invention.

As shown in FIG. 2, the measuring apparatus is provided with a scale 1, a container 2, an air-inhaling pipe, a tube 4, a glass filter 6 (which has an average pore diameter of 100 µm to 120 µm), and a measuring section 5. The container 2, having a prescribed capacity, is placed on the scale 1. The measuring section is placed on the glass filter 6. The container 2 has an opening 2a on its top, and an opening 2b on its side. The air-inhaling pipe 3 is connected with the opening 2a, while the tube 4 is connected to the opening 2b.

Moreover, in the container 2, a physiological saline 12 (for composition, see (Absorbency Without Pressure (CRC) of Particle-shape Water-Absorbing Resin material)) of a prescribed amount is placed. A lower end of the air-inhaling pipe 3 is immersed in the physiological saline 12. The glass filter 6 has a diameter of 70 mm, and is connected with the container 2 via the tube 4. Further, the glass filter 6 is so positioned that its upper portion is slightly higher than the lower end of the air-inhaling pipe 3.

The measuring section 5 is provided with a filter paper (ADVANTECH No.2) 7, a supporting cylindrical tube 8, a metal net 9, and a weight 10. The metal 9 is attached to a bottom section of the supporting cylindrical tube 8. The measuring section 5 is positioned on the glass filter 6 (which has an average pore diameter of 100 µm to 120 µm) in such a manner that the filter 7 and the supporting cylindrical tube 8 (that is, the metal net 8) are placed on the glass filter 6 in this order. Inside the supporting cylindrical tube 8, the weight 10 is placed on the metal net 9. The supporting cylindrical tube 8 is 60 mm in internal diameter. The metal net 9 is made of stainless steel, and is of 400 mesh (mesh size: 38 µm). On the metal net 9, a particle-shape water-absorbing resin material 11 of a prescribed amount is to be spread evenly. Weight of the weight 10 is adjusted so that the weight 10 can evenly apply a load of 4.83 kPa (0.7 psi) onto the metal 9, that is, onto the particle-shape water-absorbing resin material 11.

AAP of the particle-shape water-absorbing resin material 11 was measured by using the measuring apparatus thus arranged. A method for the measurement is described below.

Firstly, the physiological saline 12 was poured into the container 2, and then the prescribed preparation operation was carried out, for example, by connecting the air-inhaling pipe 3 is connected to the container 2. Next, the filter 7 is placed on the glass filter 6. Meanwhile, 0.90 g (Wp2) of the particle-shape water-absorbing resin material 11 was evenly spread inside the supporting cylindrical tube on the metal net 9. Then, the weight 10 was placed on the particle-shape water-absorbing resin material 11.

Next, weight Wc(g) of the physiological saline 12 absorbed into the particle-shape water-absorbing resin material 11 in 30 minutes after placing the supporting cylindrical tube 8 on the filter paper 7 was measured by using the scale 1. From the following equation using the weights Wp2 and Wc, Absorbency Against Pressure (AAP) (g/g) after 60 minutes from the beginning of absorption was calculated out:

Absorbency Against Pressure $(g/g)=Wc(g)/Wp2(g)$ of particle-shape water-absorbing resin material.

[Saline Flow Conductivity (SFC) of Particle-Shape Water-Absorbing Resin Material]

Saline Flow Conductivity (SFC) for a physiological saline of 0.69% by mass is a value showing liquid permeability of a water absorbent agent that has been swelled with the physiological saline of 0.69% by mass. The larger the value of SFC is, the higher the liquid permeability is. In the present Examples, SFC tests were carried out according to a saline solution Saline Flow Conductivity (SFC) test disclosed in the SFC tests described in published US patent application US 2004-0106745-A.

An apparatus shown in the US patent publication was used for the tests. Water-absorbing resin particles or their product (0.900 g) evenly spread in a counter 40 was swelled with artificial urine for 60 minutes, with 0.3 psi (2.07 kPa) applied thereon. Then, a resultant gel layer of a gel 44 was measured. Next, with a constant hydrostatic pressure, 0.69 wt % saline solution 33 was flowed through the gel layer thus swelled, while the pressure of 0.3 psi (2.07 kPa) being applied thereon, the 0.69 wt % saline solution 33 being supplied from a tank. This SFC test was carried out at the room temperature (20° C. to 25° C.). As a function of time an amount of the liquid which flowed through the gel layer was measured every 20 seconds for 10 minutes by using a computer and a scale. Flow speed Fs(T) of the liquid which has passed through the swelled gel 44 (mainly, between the particles) was determined in unit of g/s by dividing increasing weight (g) by increasing time (s). Ts is a period of time in which the constant hydrostatic pressure and stable flow speed were obtained. By using only Ts and data obtained during the ten minutes, Fs(T=0), that is, initial flow speed of the liquid which flowed through the gel layer was calculated. Fs(T=0) was calculated by extrapolating, into T=0, the result of least-squares method of Fs(T) against time. Artificial urine used here was a mixture of 0.25 g of dihydrate of calcium chloride, 2.0 g of potassium chloride, 0.50 g of hexahydrate of magnesium chloride, 2.0 g of sodium sulfide, 0.85 g of ammonium dihydrogen phosphate, 0.15 g of diammonium hydrogenphosphate, and 994.25 g of the deionized water.

EXAMPLE 1

In a kneader provided with two sigma blades, a monomer aqueous solution was prepared, the monomer aqueous solution containing sodium acrylic acid, acrylic acid, and water, and having a monomer content of 38% by weight and a neutralization ratio of 75 mol %. Into the monomer aqueous solution, polyethyleneglycoldiacrylate (average ethyleneglycol unit number: 9) was dissolved, as an internal cross-linking agent, in such an amount that polyethyleneglycoldiacrylate content was 0.03 mol % (with respect to the monomer).

Next, nitrogen gas was introduced into the monomer aqueous solution so as to reduce oxygen dissolved in the monomer aqueous solution, and replace gas inside a reactor (kneader) with the nitrogen gas. Then, a temperature of the monomer aqueous solution was adjusted to 22° C. while rotating the two sigma blade. After that, sodium persulfate and L-ascorbic acid were added as polymerization initiators to the monomer aqueous solution in such amounts that sodium persulfate and L-ascorbic acid contents became 0.12 g/mol (with respect to monomer), and 0.005 g/mol (with respect to monomer), respectively.

The polymerization was initiated instantly, so that the monomer aqueous solution became clouded. So, the rotation of the blades was stopped. When polymerization temperature reached 50° C., the rotation of the blade was resumed, so as to continue the polymerization in the kneader with stirring. After about 50 minutes, a hydrate gal-form polymer having a weight-average diameter of about 2 mm was obtained.

The thus obtained hydrate gel-form polymer was dried at 170° C. for about 60 minutes by using a hot-air dryer. Then, the thus dried polymer was pulverized by a roll mill pulverizing apparatus, and then classified by using sieves of 850 μm mesh and 180 μm mesh (so as to remove particles trapped by the sieve of 850 μm mesh and particles passed through the sieve of 180 μm). Thereby, particles (i) of water-absorbing resin having a moisture content of 3% by weight and a weight-average diameter of 400 μm. The thus obtained particles (i) of water-absorbing resin substantially included no particle having a weight-average diameter of 850 μm or larger, whereas it contained particulates having a weight-average diameter of smaller than 150 μm (due to an efficiency of the classification) by 1% by weight.

100 parts by weight of the particles (i) of water absorbing resin, and 3.23 parts by weight of a solution of surface cross-linking agent was sprayed to mix with each other by using a continuous high-speed mixer (Product Name: Turbulizer; made by Hosokawa Micron Corp.). The solution of surface cross-linking agent contains ethyleneglycoldiglycidylether, propyleneglycol, and water in a ratio of 0.03:0.5:2.7.

Figure 3:
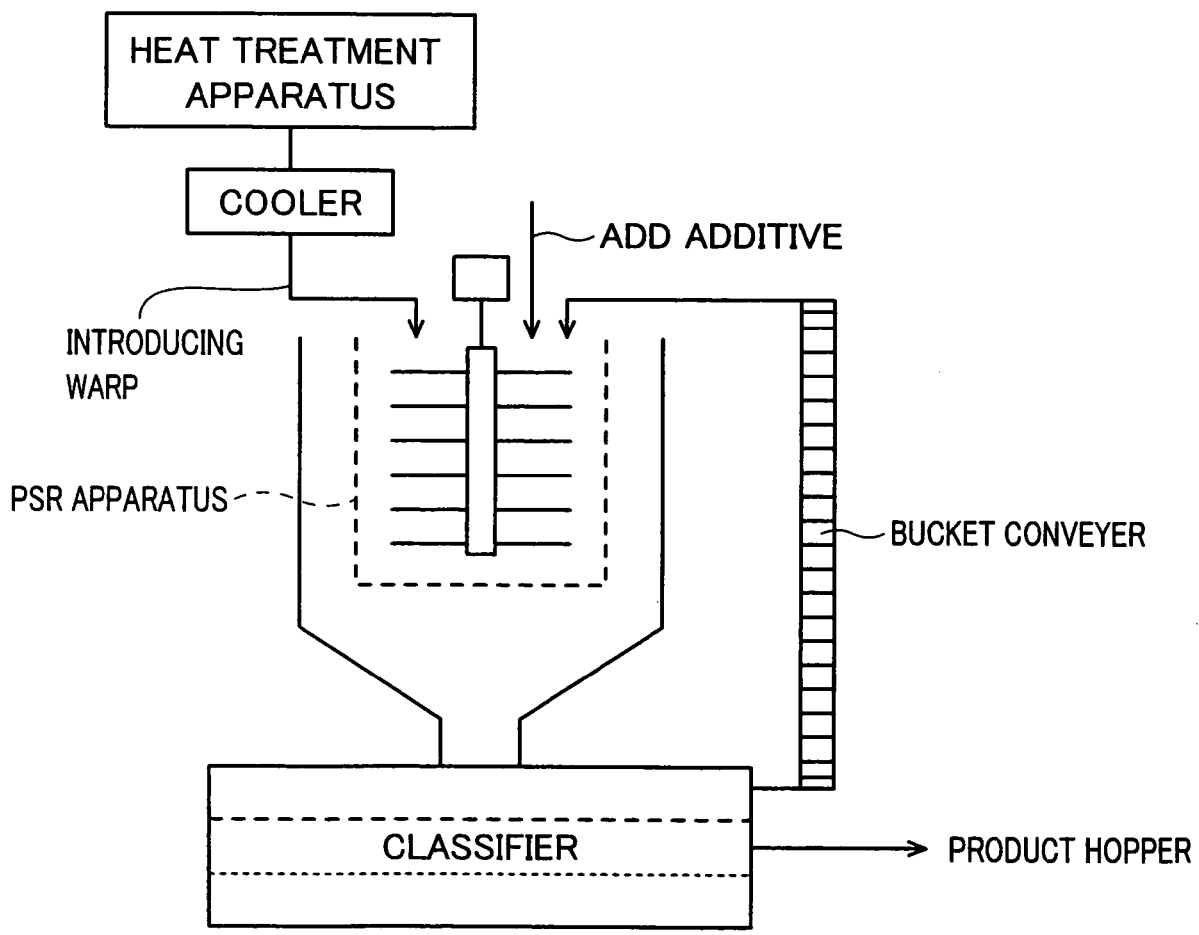
FIG. 3 a schematic view schematically showing a particle-size regulating apparatus and a classifier

The mixture of the surfactant and the particles (i) of water absorbing resin was a twin-paddle stirring dryer (Product Name: paddle dryer; available from Nara machinery Co., Ltd.; a heat treatment apparatus in FIG. 3), whose surface temperature was adjusted to 190° C. by heated steam introduced into an inside wall, a stirring panel, and rotating shafts. An average retention time was 60 minutes. Next, the mixture was cooled (average retention time was 30 minutes) by using a twin-bladed stirring dryer (a cooler in FIG. 3) in which water of 35° C. was flowed through an inside wall, a stirring panel, and rotating shafts. In this way, surface-cross-linked particles (ii) of water-absorbing resin was obtained. The particles (i) of water-absorbing resin before the surface cross-linking substantially included no particle having a weight-average diameter of 850 μm or larger (substantially zero (0% by weight), as described above. However, the particles (ii) of water absorbing resin after cooling included, by 40% by weight at 60° C., agglomerations (agglomerated particles) having a weight-average diameter of larger than 850 μm.

After that, the particles (ii) (WARP in FIG. 3), which include agglomerated water-absorbing resin particles, and agglomerated silica particulates (Product Name: Aerosil 200, made by Japan Aerosil Co., Ltd.; having a primary particle diameter of 12 nm before agglomerated) were introduced into a particle-size regulating apparatus (PSR apparatus in FIG. 3) shown in FIG. 3. Particle-size regulating treatment for the agglomerated particles was carried out at processing rate of 100 Kg/hr. Together with the particle-size regulating treatment, mixing with the silica particulates was performed (rotation rate: 600 rpm). (The particle-size regulating treatment which was carried out together with the mixing was carried out for 5 seconds) The mixing was dry mixing in which 0.5 parts by weight of the silica particulates were mixed with 100 parts by weight of the particles (ii) of water absorbing resin. Next, the mixture of the particles (ii) and the silica particulates were classified with a sieve of 850 μm mesh (the classification was carried out for 15 seconds). Particles entrapped with the sieve of 850 μm mesh was reintroduced by using a bucket conveyer, and subjected to the particle-size regulating treatment again (this particle-size regulating treatment was carried out for 5 seconds). Particles passed through the sieve of 850 μm mesh was transferred into a hopper (a production hopper in FIG. 3) by pneumatic transportation, and packed into a bag as a product (particle-shape water-absorbing resin material (1)).

The product (particle-shape water-absorbing resin material (1)) had CRC of 36(g/g), AAP of 21(g/g), and SFC of 15 ($\times 10^{-7}$ cm$^3$ s/g). Moreover, 2 g of the product (particle-shape water-absorbing resin material (1)) was put in an aluminum cup and left to stand for one hour at 25° C. under atmosphere of relative humidity of 90%. Then, the product was transferred into a JIS standard sieve of 2000 μm mesh. Weight of the particle-shape water-absorbing resin material remained on the sieve after tapping the sieve ten times, was divided by weight of the particle-shape water-absorbing resin material after left to stand for 1 hour, thereby obtaining a blocking ratio (% by weight). The blocking ratio (also called "anti-caking property") was 1% by weight.

COMPARATIVE EXAMPLE 1

The same process as Example 1 was carried out except that the particles (ii), which include the agglomerated water-absorbing resin particles after cooling were introduced into the particle-size regulating apparatus shown in FIG. 3, so as to perform the particle-size regulating treatment of the particles (ii). Then, the particles (ii) was classified with the sieve of 850 μm mesh. Particles entrapped with the sieve of 850 μm mesh was reintroduced into the particle-size regulating apparatus and again subjected to the particle-size regulating treatment. Into the particles (ii) passed through the sieve of 850 μm mesh, 0.5 parts by weight (with respect to 100 parts by weight of the particles (ii)) of the silica particulates used in Example 1 were continuously mixed by continuous mixing by using a high-speed paddle mixer having a plurality of paddles (rotation rate 1000 rpm), thereby obtaining a comparative particle-shape water-absorbing resin material (a).

The thus obtained comparative particle-shape water-absorbing resin material (a) had CRC of 36(g/g), AAP of 19(g/g), SFC of 12 ($\times 10^{-7}$ cm$^3$ s/g). From those results, it was found that the thus obtained comparative particle-shape water-absorbing resin material (a) was partially powdered, that is, "dusting" of the silica particulates occurred because it was failed to mix the particles (ii) and the silica particulates uniformly. Moreover, a blocking ratio of the comparative particle-shape water-absorbing resin material (a) was obtained in the same manner as in Example 1. The blocking ratio of the comparative particle-shape water-absorbing resin material (a) was 15% by weight.

COMPARATIVE EXAMPLE 2

The same process as Example 1 was carried out except that the surfaced-treated particles (ii) were subjected to the particle-size regulating treatment without adding the silica particulates as the additive, thereby obtaining a comparative particle-shape water-absorbing resin material (b) having no additive. The comparative particle-shape water-absorbing resin material (b) had CRC of 36(g/g), AAP of 22(g/g), SFC of 2($\times 10^{-7}$ cm$^3$ s/g), and a blocking ratio of 90% by weight.

COMPARATIVE EXAMPLE 3

The same process as Comparative Example 1 was carried out except that the surface-treated particles (ii) of water-absorbing resin, which had not subjected to the particle-size regulating treatment, were mixed with 0.5 parts by weight (with respect to 100 parts by weight of the particles (ii)) of the silica particulates as the additive, thereby obtaining a particle-shape water-absorbing resin material (c). The thus obtained particle-shape water-absorbing resin material (c) included particles having a weight-average particle size of 850 μm or larger. It was possible to feel existence of "large particles" in the particle-shape water-absorbing resin material (c).

EXAMPLE 2

The same process as Example 1 was carried out except that instead of the silica particulates, 0.01 parts by weight of diethylenepentaaminepentacetic acid (average diameter of 80 μm), which was a chelating agent, was added. Thereby a particle-shape water-absorbing resin material (2) according to the present invention was obtained. The particle-shape water-absorbing resin material (2) had CRC of 36(g/g), and AAP of 24(g/g).

Moreover, in a 50 ml beaker, 1 g of the particle-shape water-absorbing resin material (2) was swelled with 25 g of a physiological saline containing L-ascorbic acid by 0.05%, and then left to stand at 37° C. for 24 hours. A swelled gel thus obtained retained its shape and was kept solidified (not-flowable) even after 24 hours.

For the purpose of comparison, water-absorbing resin particles (comparative particle-shape water-absorbing resin material (b)) into which diethylenepentaaminepentacetic acid was not mixed were left to stand in the same manner. A gel obtained from these water-absorbing resin particles were deteriorated to be partly dissolved and became flowable and slimy.

EXAMPLE 3

The same process as Example 1 was carried out except that instead of the silica particulates, 0.5 parts by weight of activated carbon (average diameter of 100 μm) was added. Thereby a particle-shape water-absorbing resin material (3) according to the present invention was obtained. The particle-shape water-absorbing resin material (3) had CRC of 36(g/g), and AAP of 24(g/g).

Moreover, in a 50 ml beaker, 1 g of the particle-shape water-absorbing resin material (3) was swelled with 25 g of adult urine, and then left to stand at 37° C. for 24 hours, and then smelled. Smell of urine was almost undetectable.

EXAMPLE 4

The same process as Example 1 was carried out except that instead of the silica particulates, 0.8 parts by weight of aluminum sulfate 14 to 18 water (average diameter of 300 μm) was added. Thereby a particle-shape water-absorbing resin material (4) according to the present invention was obtained. The particle-shape water-absorbing resin material (4) had CRC of 36(g/g), and AAP of 24(g/g).

Absorption rate of the particle-shape water-absorbing resin material (4) was measured in accordance with JIS K7224 (1996). The absorption rate of the particle-shape water-absorbing resin material (4) was 46 seconds. For the purpose of comparison, absorption rate of water-absorbing resin particles (comparative particle-shape water-absorbing resin material (b)) into which diethylenepentaaminepentacetic acid was not mixed was measured. The absorption rate of the water-absorbing resin particles was 60 seconds.

EXAMPLE 5

The same process as Example 1 was carried out except that instead of the silica particulates, 1 parts by weight of cellulose powder (Product Name: KC flock, made by Nippon Paper Industries Co. Ltd.) was added. Thereby a particle-shape water-absorbing resin material (5) according to the present invention was obtained. The particle-shape water-absorbing resin material (5) had CRC of 36(g/g), and AAP of 24(g/g).

Moreover, absorption rate of the particle-shape water-absorbing resin material (5) was measured in accordance with JIS K7224. The absorption rate of the particle-shape water-absorbing resin material (5) was 52 seconds.

EXAMPLE 6

The same process as Example 1 was carried out except that instead of the silica particulates, 0.1 parts by weight of calcium stearate was added. Thereby a particle-shape water-absorbing resin material (6) according to the present invention was obtained. The particle-shape water-absorbing resin material (6) had CRC of 36(g/g), AAP of 22(g/g), and a blocking ratio of % by weight.

EXAMPLE 7

The same process as Example 1 was carried out except that the amount of the internal cross-linking agent was 0.10 mol %. The polymerization, pulverization, and classification were performed in the same manner as in Example 1. Thereby, particles (iii) of water absorbing resin were obtained. The particles (iii) were subjected to surface treatment with 3.23 parts by weight of a solution of a surface cross-linking agent containing ethyleneglycoldiglycidylether, propyleneglycol, and water in a ratio of 0.03:0.5:2.7. Thereby particles (iv) of water-absorbing resin were obtained. The particles (iii) before the surface cross-linking had substantially no particles (0% by weight) having a weight-average diameter of 850 μm or larger, as in the other Examples shown above. However, the particles (iv) contained, by 20% by weight, agglomerations (agglomerated particles) having a weight-average diameter of 850 μm or larger.

After that, in the same manner as in Example 1, 0.5 parts by weight of the silica particulates were added in 100 parts by weight of the particles (iv), which contained the agglomerated particles. Then, they were subjected to the particle-size regulating treatment (which was carried out for 5 seconds), in which the mixing with the silica particulates was performed together. Thereby a particle-shape water-absorbing resin material (7) according to the present invention was obtained. The particle-shape water-absorbing resin material (7) had CRC of 36(g/g), AAP of 22(g/g), and a blocking ratio of % by weight.

EXAMPLE 8

The same process as Example 1 was carried out except that the thus obtained particle-shape water-absorbing resin material (1) was further stirred for 20 minutes by using a batch-type mixer, thereby more uniformly mixing the silica particulates with the particle-shape water-absorbing resin material (8). The particle-shape water-absorbing resin material (8) was further mixed for 20 minutes in an additional mixing step, thereby more uniformly mixing the silica particulates with the particle-shape water-absorbing resin material (8). The thus obtained particle-shape water-absorbing resin material (8) had CRC and AAP equivalent to those of the particle-shape water-absorbing resin material (1). However, the particle-shape water-absorbing resin material (8) had SFC of 12 ($\times 10^{-7}$ cm$^3$ s/g), and blocking ration of 10% by weight, which were lower than those of the particle-shape water-absorbing resin material (1).

EXAMPLE 9

The same process as Example 7 was carried out except that the particle-shape water-absorbing resin material (7) was further mixed for 20 minutes by using a batch-type mixer, thereby obtaining a particle-shape water-absorbing resin material (9) more uniformly mixed with the agglomerated silica particulates. The particle-shape water-absorbing resin material (9) was further mixed for 20 minutes in an additional mixing step, thereby more uniformly mixing the silica particulates with the particle-shape water-absorbing resin material (9). The thus obtained particle-shape water-absorbing resin material (9) had CRC and AAP equivalent to those of the particle-shape water-absorbing resin material (7). However, the particle-shape water-absorbing resin material (8) had SFC of 110 ($\times 10^{-7}$ cm$^3$ s/g), and blocking ratio of 10% by weight, which were lower than those of the particle-shape water-absorbing resin material (7).

EXAMPLE 10

To water-absorbing resin particles that had been subjected to surface cross linking and particle-size regulating treatment (time for the particle-size regulating treatment: 5 seconds), inorganic particulates (agglomerated silica particulates/ Aerosil 200) of 0.5% by weight. Then, they were mixed by rotary stirring mixing. CRC and AAP were substantially constant (variation was ±0.5 g/g) regardless of how long mixing time was. However, SFC and blocking ratio were reduced as the mixing time was prolonged. SFC was 220 at 0.2 minutes, 190 at 1 minutes, 160 at 3 minutes, 150 at 10 minutes, 110 at 30 minutes (which corresponded to Example 4). Moreover, the blocking ratio was deteriorated from 1% by weight (0.2-minute mixing) to 30% by weight (30-minute mixing). It is a conventional common sense that the long-time mixing (normally several ten minutes to several hours) attains uniform mixing of the particles and the additive so as to give a particle-shape water-absorbing resin material with high property. However, on the contrary to the conventional common sense, it was found that the property (especially the liquid permeability or blocking rate attained by the inorganic powder) is improved by arranging that the mixing step (D) and the particle-size regulating step (B) are performed within 10 minutes in total.

The particle-shape water-absorbing resin material obtained by the producing method according to the present invention, which has an excellent absorbing property, is suitably applicable to, for example: hygienic/sanitary materials (body fluid absorbing products) such as paper diapers, sanitary napkins, incontinent pad, wound protecting materials, wound healing materials; absorbing products for use in absorbing pet animal urine and the like; civil engineering/construction materials such as moisture holding material for construction/civil engineering, waterproof materials, gel pusule, and the like; products for food products, such as drip absorbing materials, freshness keeping materials, cold insulator, and the like; various industrial products, such as oily water separating materials, dew inhibiting materials, coagulating materials, and the like; agricultural/horticultural products, such as water retaining materials for plants, soil, etc.; and the like applications.

Note that the method according to the present invention may be so arranged that the surface-treated particles include agglomerations and/or large particles, a weight-average diameter of the agglomerations and/or large particles being 850 µm or larger. With this arrangement, even if the water-absorbing resin particles include agglomerations (agglomerated particles) and/or large particles, the weight-average diameter of the agglomerations and/or large particles being 850 µm or larger, it is possible to break apart the agglomerations and the large particles into initial primary water-absorbing resin particles by the particle-size regulating treatment.

Moreover, the method according to the present invention preferably includes, after the step (B), the step of (E) classifying the particles into regulated particles and non-regulated particle, the regulated particles being particles whose diameter has been successfully regulated by the particle-size regulating treatment, and non-regulated particles being particles whose diameter the particle-size regulating treatment failed to regulate. (In other words, the method according to the present invention preferably includes, after the step (B), the step of (E) classifying the particles into the regulated particles and the non-regulated particles, the regulated particles having a diameter smaller than a predetermined diameter after the particle-size regulating treatment, and the non-regulated particles having a diameter equal to or larger than the predetermined diameter after the particle-size regulating treatment.) Furthermore, the method according to the present invention preferably includes, after the step (B), the step of repeating the step (B) with the non-regulated particles.

With this arrangement, it is possible to separate the agglomerations and/or large particles that are not broken apart to be primary particles, and remained after step (B), and to perform another particle-size regulating treatment (to repeat the step (B) with the non-regulated particles), that is, reintroduce into the step (B), the non-regulated particles. Moreover, it is possible to arrange to have the step (E) in order to separate, from the particle-shape water-absorbing resin material having a weight-average diameter within the preferable range, the particle-shape water-absorbing resin material having a weight-average diameter out of the preferable range. Therefore, it is possible to pulverize/separate off all the agglomerations and the large particles. This makes it possible to attain the particle-shape water-absorbing resin material having the weight-average diameter within the preferable range.

Further it is possible to have a longer retention time for the step (B) (particle-size regulating treatment (pulverization and/or classification), in the arrangement in which the step (E) (classification) is included in addition to the step (B) and the step (D) (mixing).

In the arrangement in which the particle-shape water-absorbing resin material is further classified after the particle-size regulating treatment, the particle-shape water-absorbing resin material is further mixed by vibration given to the particle-shape water-absorbing resin material during the classification. Therefore, by mixing the particle for a longer time by using a classifying apparatus (for example, a sieve) that does not give a large damage to the particles, it is possible to more uniformly mix the particle-shape water-absorbing resin material (the additive and the water-absorbing resin particles).

Moreover, the method according to the present invention is preferably arranged such that the step (C) is performed before or in the step (B). With this arrangement, it is possible to reduce the time necessary for the step (B) and the step (D). As a result, it is possible to reduce the damage on the surfaces of the particle-shape water-absorbing resin material due to the particle-size regulating apparatus.

The method according to the present invention is preferably arranged such that the additive is an inorganic powder. With this arrangement, compared with the conventional method, the inorganic powder (especially the agglomerated powder) among the various kinds of additive to use, gives remarkable effect (especially improvement of the liquid permeability or anti-blocking property (also called anti-caking property) when used as the additive.

The method according to the present invention is preferably arranged such that the particle-shape water-absorbing resin material has Absorbency Against Pressure of 10 g/g or more, or Saline Flow Conductivity of 10 (×10−7 cm3 s/g) or more. With this arrangement, it is possible to attain a particle-shape water-absorbing resin material having a higher property, showing the advantage of the present invention over the conventional method.

The method according to the present invention is preferably arranged such that the step (A) is followed by the step (B). With this arrangement, the damage is reduced, thereby attaining higher property.

The method according to the present invention is preferably arranged such that the cross-linking agent is an aqueous solution of a dehydration esterification cross-linking agent. With this arrangement, the water-absorbing resin particles having a higher property and being more safe. Further, according to the method of the present invention, it is possible to solve problems associated with the dehydration cross linking agent.

The method according to the present invention is preferably arranged such that in the step (D), the particles have a temperature in a range of 35° C. to 100° C. With this arrangement, in which in the step (D), the particles have a temperature in a temperature range, it is possible to improve flowability of the particles and prevent the particles from adhering to the apparatus, thereby attaining more uniform mixing of the particles and the additive, and continuous operability (efficiency in continuous process). As a result, it is possible to attain the particle-shape water-absorbing resin material having a high property.

The method of the present invention of producing the particle-shape water-absorbing resin material is preferably arranged such that an amount of production per production line is 100 kg/hr or more. With this arrangement, the properties of the water-absorbing resin particles will not be deteriorated even if the method is applied to a large-scale continuous production. Therefore, it is possible to produce, with efficiency and in a large quantity, the particle-shape water-absorbing resin material having high properties.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A method of producing a particle-shape water-absorbing resin material, comprising:
    (A) performing surface treatment in which surfaces of water-absorbing resin particles are cross-linked by using a cross-linking agent;
    (B) performing a particle-size regulating treatment on the surface-treated water-absorbing resin particles using a rotary particle-size regulating apparatus or a rotary continuous size particle controlling apparatus;
    (C) adding an additive to the surface-treated water-absorbing resin particles; and
    (D) dry mixing the additive and the surface-treated water-absorbing resin particles,
    wherein the particle-size regulating treatment and the dry mixing of the additive and the surface-treated water-absorbing resin particles are performed within 10 minutes in total.

2. The method as set forth in claim 1, wherein the surface-treated water-absorbing resin particles include agglomerations and large particles, a weight-average diameter of the agglomerations and large particles being 850 μm or larger based on a Japanese Industrial Standards (JIS) standard sieve.

3. The method as set forth in claim 1, further comprising:
    (E) classifying the surface-treated water-absorbing resin particles into regulated particles and non-regulated particles, the regulated particles being particles whose diameter has been successfully regulated by the particle-size regulating treatment, and the non-regulated particles being particles whose diameter the particle-size regulating treatment failed to regulate, after performing the particle-size regulating treatment.

4. The method as set forth in claim 3, further comprising performing a particle-size regulating treatment on the non-regulated particles, after performing the particle-size regulating treatment on the surface-treated water-absorbing resin particles.

5. The method as set forth in claim 1, wherein the additive is an inorganic powder.

6. The method as set forth in claim 1, wherein the particle-shape water-absorbing resin material, at 0.7 psi, has a Absorbency Against Pressure of not less than 15 g/g and not more than 80 g/g, or a Saline Flow Conductivity of $10(\times 10^{-7} cm^3 s/g)$ or more.

7. The method as set forth in claim 1, wherein the cross-linking agent is a dehydration esterification cross-linking agent and is subjected to a heating treatment at a temperature in a range of 80° C. to 230° C.

8. The method as set forth in claim 1, wherein the surface-treated water-absorbing resin particles of step (D) have a temperature in a range of 35° C. to 100° C.

9. A method of producing a particle-shape water-absorbing resin material, comprising:
    (A) performing surface treatment in which surfaces of water-absorbing resin particles are cross-linked by using a cross-linking agent;
    (B) performing a particle-size regulating treatment on the surface-treated water-absorbing resin particles;
    (C) adding an additive to the surface-treated water-absorbing resin particles; and
    (D) dry mixing the additive and the surface-treated water-absorbing resin particles,
    wherein the surface-treated water-absorbing resin particles are pulverized and classified in the particle-size regulating treatment, and
    the particle-size regulating treatment and the dry mixing of the additive and the surface-treated water-absorbing resin particles are performed within 10 minutes in total.

10. The method as set forth in claim 9, wherein the surface-treated water-absorbing resin particles include agglomerations and large particles, a weight-average diameter of the agglomerations and large particles being 850 μm or larger based on a Japanese Industrial Standards (JIS) standard sieve.

11. The method as set forth in claim 9, further comprising:
    (E) classifying the surface-treated water-absorbing resin particles into regulated particles and non-regulated particles, the regulated particles being particles whose diameter has been successfully regulated by the particle-size regulating treatment, and the non-regulated particles being particles whose diameter the particle-size regulating treatment failed to regulate, after performing the particle-size regulating treatment.

12. The method as set forth in claim 11, further comprising repeating the particle-size regulating treatment with the non-regulated particles, after performing the particle-size regulating treatment on the surface-treated water- absorbing resin particles.

13. The method as set forth in claim 9, wherein performing the particle-size regulating treatment and mixing of the additive and the surface-treated water-absorbing resin particles are performed concurrently.

14. The method as set forth in claim 9, wherein the additive is an inorganic powder.

15. The method as set forth in claim 9, wherein the particle-shape water-absorbing resin material, at 0.7 psi, has a Absorbency Against Pressure of not less than 15 g/g and not more than 80 g/g, or a Saline Flow Conductivity of $10(\times 10^{-7} cm^3 s/g)$ or more.

16. The method as set forth in claim 9, wherein the cross-linking agent is a dehydration esterification cross-linking agent and is subjected to a heating treatment at a temperature in a range of 80° C. to 230° C.

17. The method as set forth in claim 9, wherein the surface-treated water-absorbing resin particles of step (D) have a temperature in a range of 35° C. to 100° C.

18. The method as set forth in claim 1, wherein an amount of production per production line is 100 kg/hr or greater.

19. The method as set forth in claim 9, wherein an amount of production per production line is 100 kg/hr or greater.

20. The method as set forth in claim 1, wherein performing the particle-size regulating treatment includes pulverizing or classifying the surface-treated water-absorbing resin particles or agglomerations of step (B).

21. The method as set forth in claim 9, wherein performing the particle-size regulating treatment includes pulverizing or classifying the surface-treated water-absorbing resin particles or agglomerations of step (B).

22. The method as set forth in claim 1, wherein
    a weight-average diameter of the particle-shape water-absorbing resin material subjected to the particle-size regulating treatment is 280 μm to 500 μm based on a Japanese Industrial Standards (JIS) standard sieve,
    a ratio of surface-treated water-absorbing resin particles trapped by a sieve of 850 μm mesh is 1% or less by weight, and
    a ratio of surface-treated water-absorbing resin particles passing through a sieve of 150 μm mesh is 5% or less by weight.

23. The method as set forth in claim 9, wherein
a weight-average diameter of the particle-shape water-absorbing resin material subjected to the particle-size regulating treatment is 280 μm to 500 μm based on a Japanese Industrial Standards (JIS) standard sieve,
a ratio of surface-treated water-absorbing resin particles trapped by a sieve of 850 μm mesh is 1% or less by weight, and
a ratio of surface-treated water-absorbing resin particles passing through a sieve of 150 μm mesh is 5% or less by weight.

24. The method as set forth in claim 1, wherein
the surface-treated water-absorbing resin particles have an Absorbency Under No Pressure (z), an Absorbency Against Pressure (x) at 0.7 psi, and a Saline Flow Conductivity (y) wherein the expressions $20\ g/g \leq z \leq 80\ g/g$, $15\ g/g \leq x \leq 80\ g/g$, and $y \geq 1(\times 10^{-7} cm^3\ s/g)$ are satisfied.

25. The method as set forth in claim 9, wherein
the surface-treated water-absorbing resin particles have an Absorbency Under No Pressure (z), an Absorbency Against Pressure (x) at 0.7 psi, and a Saline Flow Conductivity (y) wherein the expressions $20\ g/g \leq z \leq 80\ g/g$, $15\ g/g \leq x \leq 80\ g/g$, and $y \geq 1(\times 10^{-7} cm^3\ s/g)$ are satisfied.

26. The method as set forth in claim 1, wherein the additive is a water-insoluble inorganic powder.

27. The method as set forth in claim 9, wherein the additive is a water-insoluble inorganic powder.

28. A method of producing a particle-shape water-absorbing resin material, comprising:
(A) performing surface treatment in which surfaces of water-absorbing resin particles are cross-linked by using a cross-linking agent;
(B) performing a particle-size regulating treatment on the surface-treated water-absorbing resin particles;
(C) adding an additive to the surface-treated water-absorbing resin particles; and
(D) dry mixing the additive and the surface-treated water-absorbing resin particles;
wherein the addition of the additive and the particle-size regulating treatment are performed simultaneously, and
performing the particle-size regulating treatment includes the dry mixing of the additive and the surface-treated water-absorbing resin particles.

* * * * *